US011759456B2

(12) United States Patent
Sugimoto et al.

(10) Patent No.: US 11,759,456 B2
(45) Date of Patent: Sep. 19, 2023

(54) PHARMACEUTICAL COMPOSITION

(71) Applicant: KOWA COMPANY, LTD., Nagoya (JP)

(72) Inventors: Shin Sugimoto, Fuji (JP); Akito Minamizono, Fuji (JP)

(73) Assignee: KOWA COMPANY, LTD., Nagoya (JP)

( * ) Notice: Subject to any disclaimer, the term of this patent is extended or adjusted under 35 U.S.C. 154(b) by 589 days.

(21) Appl. No.: 16/627,128

(22) PCT Filed: Jun. 29, 2018

(86) PCT No.: PCT/JP2018/024886
§ 371 (c)(1),
(2) Date: Dec. 27, 2019

(87) PCT Pub. No.: WO2019/004451
PCT Pub. Date: Jan. 3, 2019

(65) Prior Publication Data
US 2020/0179346 A1   Jun. 11, 2020

(30) Foreign Application Priority Data
Jun. 30, 2017   (JP) .............................. JP2017-129147

(51) Int. Cl.
    A61K 31/423   (2006.01)
    A61K 9/20     (2006.01)
    A61K 47/02    (2006.01)
    A61K 47/20    (2006.01)
    A61K 47/26    (2006.01)
    A61K 47/32    (2006.01)
    A61K 47/38    (2006.01)

(52) U.S. Cl.
    CPC .............. *A61K 31/423* (2013.01); *A61K 9/20* (2013.01); *A61K 47/02* (2013.01); *A61K 47/20* (2013.01); *A61K 47/26* (2013.01); *A61K 47/32* (2013.01); *A61K 47/38* (2013.01)

(58) Field of Classification Search
    CPC ........ A61K 31/423; A61K 9/20; A61K 47/02; A61K 47/20; A61K 47/26; A61K 47/32; A61K 47/38
    USPC ....................................................... 514/375
    See application file for complete search history.

(56) References Cited

U.S. PATENT DOCUMENTS

| 2005/0101636 A1 | 5/2005 | Yamazaki et al. |
| 2015/0196538 A1 | 7/2015 | Takizawa et al. |
| 2016/0136138 A1 | 5/2016 | Shibata et al. |

FOREIGN PATENT DOCUMENTS

| JP | 2015-515498 A   | 5/2015 |
| JP | WO2019/004451 A1 | 1/2019 |
| JP | 2022-82821 A    | 6/2022 |
| WO | WO 2005/023777 A1 | 3/2003 |
| WO | WO 2014/050134 A1 | 4/2014 |
| WO | WO 2014/065427 A1 | 5/2014 |
| WO | WO 2015/005365 A1 | 1/2015 |

OTHER PUBLICATIONS

Office Action dated Jun. 14, 2022, in corresponding Japanese Patent Application No. 2018-126050 (with English Translation), 11 pages.
International Search Report dated Aug. 21, 2018 in PCT/JP2018/024886 filed Jun. 29, 2018, 2 pages.
Report on the deliberation results of parmodia tablets 0.1 mg, Pharmaceutical Evaluation Division of Pharmaceutical Safety and Environmental Health Bereau, Ministry of Health, Labour and Welfare, Jul. 3, 2017, (with partial English translation (pp. 5-6)).
Yamazaki et al., "Enantioselective Synthesis of the PPARα Agoinst®-K-13675 via (S)-Hydroxybutyrolactone", Synthesis, 2008 (7), 1017-1012.
Fruchart JC., "Selective peroxisome proliferator-activated receptorα modulators (SSPARMα): The next generation of peroxisome proliferator-activated receptor α-agoinists" Cardiovasc Diabetol., 2013; 12:82.
Office Action dated Mar. 30, 2021 in corresponding Japanese Patent Application No. 2019-527074 (with English Translation), 8 pages.
Wakiyama Naoki, "Stability and Shelf Life of Pharmaceuticals", Materials Life, vol. 3, No. 2, Apr. 1991, pp. 104-109, (with partial English machine translation).

*Primary Examiner* — Michael Barker
(74) *Attorney, Agent, or Firm* — Oblon, McClelland, Maier & Neustadt, L.L.P.

(57) ABSTRACT

Provided is a pharmaceutical composition containing pemafibrate, a salt thereof or a solvate thereof and having excellent homogeneity. The pharmaceutical composition contains pemafibrate, a salt thereof or a solvate thereof in an amount of 0.017 to 4.2 mass % in terms of a free form of pemafibrate with respect to the total mass of the pharmaceutical composition.

18 Claims, No Drawings

PHARMACEUTICAL COMPOSITION

FIELD OF THE INVENTION

The present invention relates to a pharmaceutical composition etc.

BACKGROUND OF THE INVENTION

It is known that pemafibrate (Chemical Name: (2R)-2-[3-([1,3-Benzoxazol-2-yl[3-(4-methoxyphenoxy)propyl]amino]methyl)phenoxy]butanoic acid) (International Nonproprietary Name: pemafibrate) represented by the following structural formula:

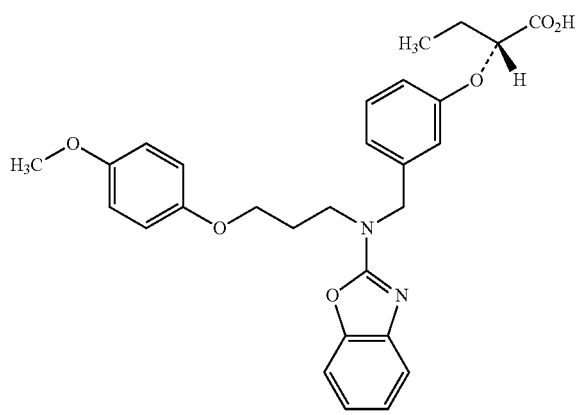

a salt thereof or a solvate thereof has excellent PPAR-α agonist activity, exhibits plasma triglyceride concentration reducing action, HDL cholesterol increasing action, etc., and is useful for prevention and treatment of dyslipidemia (hyperlipidemia) (Patent Document 1 and Non-Patent Documents 1 and 2), and useful for prevention and treatment of NAFLD (non-alcoholic fatty liver disease) (Patent Document 2).

Meanwhile, a compound useful as an active component for a pharmaceutical preparation is normally formulated as some pharmaceutical composition and supplied, and from the viewpoint of reliably exhibiting expected drug efficacy and avoiding unanticipated adverse side effects, it is very important that the pharmaceutical composition to be supplied maintains a certain level of quality without variations such as lot-to-lot variation.

PRIOR ART DOCUMENTS

Patent Documents

Patent Document 1: International Publication No. WO 2005/023777
Patent Document 2: International Publication No. WO 2015/005365

Non-Patent Documents

Non-Patent Document 1: YukiyoshiYamazaki, et al., Synthesis, 2008(7), 1017-1022.
Non-Patent Document 2: Fruchart J C., Cardiovasc Diabetol., 2013; 12: 82.

SUMMARY OF THE INVENTION

Problems to be Solved by the Invention

However, manufacturability of pharmaceutical compositions, such as homogeneity, significantly depends on the physical and chemical properties of components, but it is often impossible to predict such properties from the chemical structures of the components, and there are not a few cases where a problem becomes evident only when a pharmaceutical composition is actually produced. Thus, establishment of a technique for securing homogeneity of a pharmaceutical composition commonly requires considerable try and error.

Pemafibrate, a salt thereof or a solvate thereof has been only reported to exhibit the above-described pharmacological effects, and has heretofore not been specifically studied in terms of a pharmaceutical composition, and manufacturability such as homogeneity of the pharmaceutical composition has heretofore not been reported at all.

In these circumstances, for developing a pharmaceutical composition containing pemafibrate, a salt thereof or a solvate thereof, the present inventors have first actually produced the pharmaceutical composition. In general, the content uniformity of a component in a pharmaceutical composition is good when the content of the component is high. However, very surprisingly, it has been found that the content of pemafibrate varies for each pharmaceutical composition even when the content of pemafibrate in the pharmaceutical composition is as high as more than 5 mass %, let alone as low as less than 0.01 mass %, with respect to the total mass of the pharmaceutical composition, and thus, the pharmaceutical composition is poor in homogeneity (uniformity) of the content of pemafibrate. If pharmaceutical compositions significantly differ in content of pemafibrate, there may be variations in efficacy and safety among the pharmaceutical compositions.

Thus, an object of the present invention is to provide a pharmaceutical composition containing pemafibrate, a salt thereof or a solvate thereof, and having excellent homogeneity.

Means for Solving the Problems

In order to solve the problem with the content uniformity of pemafibrate, a salt thereof or a solvate thereof in a pharmaceutical composition, the present inventors have further extensively conducted studies, and found that by making an adjustment so that the content of pemafibrate, a salt thereof or a solvate thereof in the pharmaceutical composition is within the range of 0.017 to 4.2 mass % in terms of a free form of pemafibrate with respect to the total mass of the pharmaceutical composition, the content uniformity of pemafibrate in the pharmaceutical composition is improved. The present invention has been accomplished on the basis of this finding.

Accordingly, the present invention provides a pharmaceutical composition containing pemafibrate, a salt thereof or a solvate thereof in an amount of 0.017 to 4.2 mass % in terms of a free form of pemafibrate with respect to the total mass of the pharmaceutical composition.

The present invention also provides a method for improving the content uniformity of pemafibrate, a salt thereof or a solvate thereof in a pharmaceutical composition, the method including the step of incorporating pemafibrate, a salt thereof or a solvate thereof in an amount of 0.017 to 4.2 mass % in terms of a free form of pemafibrate with respect to the total mass of the pharmaceutical composition.

Effects of the Invention

According to the present invention, it is possible to provide a pharmaceutical composition having improved content uniformity of pemafibrate in the pharmaceutical composition and having excellent homogeneity.

DETAILED DESCRIPTION OF THE INVENTION

<Pemafibrate, Salt Thereof or Solvate Thereof>

Herein, "pemafibrate, a salt thereof or a solvate thereof" includes pemafibrate (Chemical Name: (2R)-2-[3-([1,3-Benzoxazol-2-yl[3-(4-methoxyphenoxy)propyl]amino]methyl)phenoxy]butanoic acid) (International Nonproprietary Name: pemafibrate) itself, a pharmaceutically acceptable salt of pemafibrate and a solvate of pemafibrate or a pharmaceutically acceptable salt thereof with water, alcohol (for example ethanol) or the like. The pharmaceutically acceptable salt is not particularly limited, and examples thereof include acid addition salts and base addition salts. Specific examples of the acid addition salts include acid addition salts with inorganic acids, such as hydrochlorides, hydrobromides, hydroiodides, sulfate salts, nitrate salts and phosphate salts; and acid addition salts with organic acids, such as benzoate salts, methanesulfonate salts, ethanesulfonate salts, benzenesulfonate salts, p-toluenesulfonate salts, maleate salts, fumarate salts, tartrate salts, citrate salts and acetate salts. Specific examples of the base addition salts include metal salts such as sodium salts, potassium salts, lithium salts, calcium salts and magnesium salts; salts with amines such as ammonia, trimethylamine, triethylamine, pyridine, collidine and lutidine; and base addition salts with organic bases such as lysine, arginine, cinchonine and cinchonidine.

The shape, the size and the like of pemafibrate, a salt thereof or a solvate thereof are not particularly limited, and when the average particle diameter of primary particles is measured in accordance with The Japanese Pharmacopoeia, 17th Edition, Laser Diffraction Measurement of Particle Size, d50 and d90 values are preferably as follows.

d50: preferably 100 μm or less, more preferably 50 μm or less, still more preferably 20 μm or less, particularly preferably 1 to 20 μm.

d90: preferably 200 μm or less, more preferably 135 μm or less, still more preferably 80 μm or less, particularly preferably 1 to 80 μm.

Pemafibrate, a salt thereof or a solvate thereof is a known compound, and can be produced through a method as disclosed in Patent Document 1, Non-Patent Document 1 or U.S. Pat. No. 7,109,226, for example. In the present invention, a pemafibrate crystal which can be produced through the method described in Non-Patent Document 1 (preferably a crystal showing a melting point of 95 to 101° C., particularly preferably 97 to 100° C. in measurement performed in accordance with The Japanese Pharmacopoeia, 17th Edition, Melting Point Determination Method 1) is preferably used. The disclosures of the documents are incorporated herein by reference.

The content of pemafibrate, a salt thereof or a solvate thereof in the pharmaceutical composition of the present invention is 0.017 to 4.2 mass % in terms of a free form of pemafibrate with respect to the total mass of the pharmaceutical composition. By setting the content of pemafibrate, a salt thereof or a solvate thereof within this range, content uniformity is improved. From the viewpoint of improvement of content uniformity, the content is preferably 0.042 to 4.2 mass %, more preferably 0.042 to 1.7 mass %, particularly preferably 0.042 to 0.83 mass %.

The content of pemafibrate, a salt thereof or a solvate thereof per dosage unit of the pharmaceutical composition may be adjusted in appropriate consideration of the above-described content of the pharmaceutical composition, and the dosage form, the size and the like of the pharmaceutical composition, but is, for example, preferably 0.02 to 5 mg, particularly preferably 0.05 to 1 mg, in terms of a free form of pemafibrate. When the pharmaceutical composition of the present invention is a tablet, the content of pemafibrate, a salt thereof or a solvate thereof per tablet is also preferably 0.02 to 5 mg, particularly preferably 0.05 to 1 mg, in terms of a free form of pemafibrate.

The content of pemafibrate, a salt thereof or a solvate thereof can be determined by, for example, performing measurement on the pharmaceutical composition by HPLC.

Further one or more selected from the group consisting of the following components may be optionally incorporated in the pharmaceutical composition of the present invention.

Component 1: cellulose ether species
Component 2: starch species
Component 3: povidone species
Component 4: silicic acid compound
Component 5: polyhydric alcohol
Component 6: alkyl sulfate ester
Component 7: disaccharide species
Component 8: cellulose By incorporating the above-described components in the pharmaceutical composition, the content uniformity of pemafibrate is improved.

<Cellulose Ether Species>

Herein, the "cellulose ether species" means one or more selected from the group consisting of a compound in which all or some of hydroxy groups of cellulose form ether bonds; and a salt thereof. The cellulose ether species may be cellulose to which in addition to etherification, further modification such as esterification or crosslink formation as necessary has been applied. Here, the salt is not particularly limited, and specific examples thereof include alkali metal salts such as sodium salts and potassium salts; and salts with metals of Group 2 elements, such as calcium salts and magnesium salts. The average degree of polymerization, the form (crystal form) and the like of the cellulose ether species are not particularly limited, and the average degree of polymerization is preferably 10 to 10,000.

Specific examples of the cellulose ether species include alkylcelluloses or salts thereof such as methylcellulose and ethylcellulose; hydroxyalkylcelluloses or salts thereof such as hydroxyethylcellulose and hydroxypropylcellulose; alkyl (hydroxyalkyl)celluloses, derivatives (ester derivatives) thereof or salts thereof such as hydroxyethylmethylcellulose, hypromellose, hypromellose acetate succinate ester and hypromellose phthalate ester; and carboxyalkylcelluloses, derivatives (cross-linked polymers) thereof or salts thereof such as carmellose, carmellose potassium, carmellose calcium, carmellose sodium, carboxymethylethylcellulose and croscarmellose sodium, and these cellulose ethers may be used singly, or in combinations of two or more thereof. The alkyl group in the cellulose ether species is not particularly limited, and is preferably a linear or branched C1-C6 alkyl group. The degree of substitution with hydroxyalkoxy groups in the hydroxyalkylcellulose is not particularly limited, and for example, hydroxypropylcellulose includes both non-low substituted hydroxypropylcellulose and low substituted hydroxypropylcellulose. Here, the low substituted hydroxypropylcellulose refers to hydroxypropylcellulose in which the hydroxypropoxy group content determined in a dried state is 5.0 to 16.0% as described in The Japanese Pharmacopoeia, 17th Edition.

From the viewpoint of improvement of content uniformity, the cellulose ether species is preferably one or more selected from the group consisting of an alkylcellulose, a hydroxyalkylcellulose, an alkyl(hydroxyalkyl)cellulose, a carboxyalkylcellulose, a cross-linked polymer of a carboxyalkylcellulose and a salt thereof, more preferably one or more selected from the group consisting of a C1-C6 alkylcellulose, a hydroxy C1-C6 alkylcellulose, a C1-C6 alkyl(hydroxy C1-C6 alkyl)cellulose, a carboxy C1-C6 alkylcellulose, a cross-linked polymer of a carboxy C1-C6 alkylcellulose and a salt thereof, still more preferably one or more selected from the group consisting of methylcellulose, ethylcellulose, hydroxypropylcellulose, hypromellose, carmellose, croscarmellose and a salt thereof, yet more preferably one or more selected from the group consisting of methylcellulose, ethylcellulose, hydroxypropylcellulose, hypromellose, carmellose, carmellose potassium, carmellose calcium, carmellose sodium and croscarmellose sodium, particularly preferably one or more selected from the group consisting of methylcellulose, hydroxypropylcellulose, hypromellose, carmellose, carmellose calcium, carmellose sodium and croscarmellose sodium. The hydroxypropylcellulose is preferably low substituted hydroxypropylcellulose. From the viewpoint of ease of production of a pharmaceutical composition (particularly a solid preparation), the cellulose ether species is preferably solid at normal temperature (any temperature in the range of 15 to 25° C.).

Each of these cellulose ether species is a known component. The cellulose ether species may be produced through a known method, or commercially available products may be used. Examples of the commercially available products include ETHOCEL (Dow Chemical Japan Limited), CMEC (Freund Corporation), NS-300 (San-Ei Gen F.F.I., Inc.), ECG-505 (San-Ei Gen F.F.I., Inc.), CELLOGEN (San-Ei Gen F.F.I., Inc.), Ac-Di-Sol (Asahi Kasei Corporation), HEC (Sumitomo Seika Chemicals Co., Ltd.), Hydroxypropylcellulose (Nippon Soda Co., Ltd.), Shin-Etsu AQOAT (Shin-Etsu Chemical Co., Ltd.), METOLOSE 90SH-SR (Shin-Etsu Chemical Co., Ltd.), HPMCP (Shin-Etsu Chemical Co., Ltd.), METOLOSE SM (Shin-Etsu Chemical Co., Ltd.), TC-5 (San-Ei Gen F.F.I., Inc.) and L-HPC (Shin-Etsu Chemical Co., Ltd.).

When cellulose ether species are used, the content of the cellulose ether species in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the cellulose ether species with respect to the total mass of the pharmaceutical composition is preferably 0.5 to 30 mass %, more preferably 1 to 20 mass %, still more preferably 1.5 to 15 mass %, particularly preferably 2 to 10 mass %.

When alkylcelluloses or salts thereof are used as cellulose ether species, the content of the alkylcelluloses or salts thereof with respect to the total mass of the pharmaceutical composition is preferably 0.6 to 22 mass %, more preferably 1.1 to 19 mass %, particularly preferably 3 to 8 mass %, from the viewpoint of improvement of content uniformity.

When hydroxyalkylcelluloses or salts thereof are used as cellulose ether species, the content of the hydroxyalkylcelluloses or salts thereof with respect to the total mass of the pharmaceutical composition is preferably 0.7 to 24 mass %, more preferably 1.2 to 18 mass %, particularly preferably 3 to 8 mass %, from the viewpoint of improvement of content uniformity.

When alkyl(hydroxyalkyl)celluloses, derivatives thereof or salts thereof are used as cellulose ether species, the content of the alkyl(hydroxyalkyl)celluloses, derivatives thereof or salts thereof with respect to the total mass of the pharmaceutical composition is preferably 0.8 to 26 mass %, more preferably 1.3 to 17 mass %, particularly preferably 4 to 9 mass %, from the viewpoint of improvement of content uniformity.

When carboxyalkylcelluloses, derivatives thereof or salts thereof are used as cellulose ether species, the content of the carboxyalkylcelluloses, derivatives thereof or salts thereof with respect to the total mass of the pharmaceutical composition is preferably 0.9 to 28 mass %, more preferably 1.4 to 16 mass %, particularly preferably 1.6 to 9 mass %, from the viewpoint of improvement of content uniformity.

When cellulose ether species are used, the mass ratio between the content of pemafibrate, a salt thereof or a solvate thereof and the content of the cellulose ether species in the pharmaceutical composition is not particularly limited, and from the viewpoint of improvement of content uniformity, the total content of the cellulose ether species with respect to 1 part by mass of a free form of pemafibrate is preferably 3 to 200 parts by mass, more preferably 5 to 150 parts by mass, particularly preferably 10 to 100 parts by mass.

When alkylcelluloses or salts thereof are used as cellulose ether species, the mass ratio between the content of pemafibrate, a salt thereof or a solvate thereof and the content of the alkylcelluloses or salts thereof in the pharmaceutical composition is not particularly limited, and from the viewpoint of improvement of content uniformity, the total content of the alkylcelluloses or salts thereof with respect to 1 part by mass of a free form of pemafibrate is preferably 4 to 160 parts by mass, more preferably 6 to 110 parts by mass, particularly preferably 20 to 60 parts by mass.

When hydroxyalkylcelluloses or salts thereof are used as cellulose ether species, the mass ratio between the content of pemafibrate, a salt thereof or a solvate thereof and the content of the hydroxyalkylcelluloses or salts thereof in the pharmaceutical composition is not particularly limited, and from the viewpoint of improvement of content uniformity, the total content of the hydroxyalkylcelluloses or salts thereof with respect to 1 part by mass of a free form of pemafibrate is preferably 4 to 170 parts by mass, more preferably 7 to 120 parts by mass, still more preferably 20 to 100 parts by mass, particularly preferably 30 to 70 parts by mass.

When alkyl(hydroxyalkyl)celluloses, derivatives thereof or salts thereof are used as cellulose ether species, the mass ratio between the content of pemafibrate, a salt thereof or a solvate thereof and the content of the alkyl(hydroxyalkyl)celluloses, derivatives thereof or salts thereof in the pharmaceutical composition is not particularly limited, and from the viewpoint of improvement of content uniformity, the total content of the alkyl(hydroxyalkyl) celluloses, derivatives thereof or salts thereof with respect to 1 part by mass of a free form of pemafibrate is preferably 4 to 180 parts by mass, more preferably 8 to 130 parts by mass, still more preferably 20 to 100 parts by mass, particularly preferably 40 to 80 parts by mass.

When carboxyalkylcelluloses, derivatives thereof or salts thereof are used as cellulose ether species, the mass ratio between the content of pemafibrate, a salt thereof or a solvate thereof and the content of the carboxyalkylcelluloses, derivatives thereof or salts thereof in the pharmaceutical composition is not particularly limited, and from the viewpoint of improvement of content uniformity, the total content of the carboxyalkylcelluloses, derivatives thereof or salts thereof with respect to 1 part by mass of a free form of pemafibrate is preferably 4 to 190 parts by mass, more preferably 9 to 140 parts by mass, still more preferably 14 to 100 parts by mass, particularly preferably 19 to 90 parts by mass.

<Starch Species>

Herein, the "starch species" means one or more selected from the group consisting of starch itself; starch in which all or some of hydroxy groups form ether bonds; a derivative thereof; and a salt thereof. The starch species include those subjected to treatment such as gelatinization or aging. The derivative includes starch or etherified products thereof in which further modification such as esterification, crosslink formation or hydrolysis is applied. Here, the salt is not particularly limited, and specific examples thereof include alkali metal salts such as sodium salts and potassium salts; and salts with metals of Group 2 elements, such as calcium salts and magnesium salts.

Specific examples of the starch species include starches or salts thereof such as pregelatinized starch, wheat starch, rice starch, corn starch, potato starch, partially pregelatinized starch, wheat flour, rice flour and semi-digested starch; hydroxyalkyl ethers of starch or salts thereof such as hydroxypropyl starch; and carboxyalkyl ethers of starch or salts thereof such as carboxymethyl starch sodium, and these starches may be used singly, or in combinations of two or more thereof. The alkyl group in the starch species is not particularly limited, and is preferably a linear or branched C1-C6 alkyl group.

From the viewpoint of improvement of content uniformity, the starch species is preferably one or more selected from the group consisting of starch, a hydroxyalkyl ether of starch, a carboxyalkyl ether of starch and a salt thereof, more preferably one or more selected from the group consisting of starch, a hydroxy C1-C6 alkyl ether of starch, a carboxy C1-C6 alkyl ether and a salt thereof, still more preferably one or more selected from the group consisting of starch, hydroxypropyl starch, carboxymethyl starch and a salt thereof, particularly preferably one or more selected from the group consisting of starch and carboxymethyl starch sodium. From the viewpoint of ease of production of a pharmaceutical composition (particularly a solid preparation), the starch species is preferably solid at normal temperature (any temperature in the range of 15 to 25° C.).

Each of these starch species is a known component. The starch species may be produced through a known method, or commercially available products may be used. Examples of the commercially available products include LYCATAB PGS (Roquette Japan K.K.), GLYCOLYS (Roquette Japan K.K.), Starch (soluble) (Kishida Chemical Co., Ltd.), Corn Starch (San-Ei Gen F.F.I., Inc.), Potato Starch (JUNSEI CHEMICAL CO., LTD.), HPS-101 (Freund Corporation) and LYCATABC (Roquette Japan K.K.).

When starch are used, the content of the starch species in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the starch species with respect to the total mass of the pharmaceutical composition is preferably 0.5 to 50 mass %, more preferably 1 to 40 mass %, still more preferably 1.5 to 30 mass %, particularly preferably 2 to 20 mass %.

When starch is used as starch species, the content of the starch with respect to the total mass of the pharmaceutical composition is preferably 0.6 to 47 mass %, more preferably 1.1 to 38 mass %, particularly preferably 1.6 to 28 mass %, from the viewpoint of improvement of content uniformity.

When carboxyalkyl ethers of starch or salts thereof are used as starch species, the content of the carboxyalkyl ethers of starch or salts thereof with respect to the total mass of the pharmaceutical composition is preferably 0.8 to 45 mass %, more preferably 1.3 to 36 mass %, particularly preferably 1.7 to 26 mass %, from the viewpoint of improvement of content uniformity.

When starch species are used, the mass ratio between the content of pemafibrate, a salt thereof or a solvate thereof and the content of the starch species in the pharmaceutical composition is not particularly limited, and from the viewpoint of improvement of content uniformity, the total content of the starch species with respect to 1 part by mass of a free form of pemafibrate is preferably 5 to 400 parts by mass, more preferably 15 to 300 parts by mass, particularly preferably 20 to 200 parts by mass.

When starch is used as starch species, the mass ratio between the content of pemafibrate, a salt thereof or a solvate thereof and the content of the starch in the pharmaceutical composition is not particularly limited, and from the viewpoint of improvement of content uniformity, the total content of the starch with respect to 1 part by mass of a free form of pemafibrate is preferably 7 to 380 parts by mass, more preferably 16 to 280 parts by mass, particularly preferably 30 to 190 parts by mass.

When carboxyalkyl ethers of starch or salts thereof are used as starch species, the mass ratio between the content of pemafibrate, a salt thereof or a solvate thereof and the content of the carboxyalkyl ethers of starch or salts thereof in the pharmaceutical composition is not particularly limited, and from the viewpoint of improvement of content uniformity, the total content of the carboxyalkyl ethers of starch or salts thereof with respect to 1 part by mass of a free form of pemafibrate is preferably 9 to 370 parts by mass, more preferably 17 to 270 parts by mass, particularly preferably 40 to 180 parts by mass.

<Povidone Species>

Herein, the "povidone species" means polymers of 1-vinyl-2-pyrrolidone, and includes not only homopolymers of 1-vinyl-2-pyrrolidone but also copolymers of 1-vinyl-2-pyrrolidone and other polymerizable compounds. The polymer may be either a non-cross-linked polymer or a cross-linked polymer.

The K value of a linear-chain polymer of 1-vinyl-2-pyrrolidone (povidone) is not particularly limited; the indicated K value is preferably 12 to 90, particularly preferably 25 to 90.

Specific examples of the povidone species include linear-chain polymers of 1-vinyl-2-pyrrolidone, such as povidone (the K value of the povidone is not particularly limited, and the indicated K value is, for example, 12, 17, 25, 30 or 90); copolymers of 1-vinyl-2-pyrrolidone and vinyl acetate, such as copolyvidone; and cross-linked polymers of 1-vinyl-2- pyrrolidone, such as crospovidone. These povidones may be used singly, or in combinations of two or more thereof.

From the viewpoint of improvement of content uniformity, the povidone species is preferably one or more selected from the group consisting of povidone, copolyvidone and crospovidone, more preferably one or more selected from the group consisting of povidone and crospovidone, particularly preferably crospovidone. From the viewpoint of ease of production of a pharmaceutical composition (particularly a solid preparation), the povidone species is preferably solid at normal temperature (any temperature in the range of 15 to 25° C.).

Each of these povidone species is a known component. The povidone species may be produced through a known method, or commercially available products may be used. Examples of the commercially available products include Kollidon CL, Kollidon VA64 and Kollidon (each from BASF Japan Ltd.).

When povidone species are used, the content of the povidone species in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the povidone species with respect to the total mass of the pharmaceutical composition is preferably 0.1 to 20 mass %, more preferably 0.5 to 15 mass %, particularly preferably 1 to 10 mass %.

When linear-chain polymers of 1-vinyl-2-pyrrolidone are used as povidone species, the content of the linear-chain polymers of 1-vinyl-2-pyrrolidone with respect to the total mass of the pharmaceutical composition is preferably 0.2 to 16 mass %, more preferably 0.6 to 14 mass %, particularly preferably 3 to 9 mass %, from the viewpoint of improvement of content uniformity.

When cross-linked polymers of 1-vinyl-2-pyrrolidone are used as povidone species, the content of the cross-linked polymers of 1-vinyl-2-pyrrolidone with respect to the total mass of the pharmaceutical composition is preferably 0.3 to 17 mass %, more preferably 0.7 to 13 mass %, particularly preferably 2 to 8 mass %, from the viewpoint of improvement of content uniformity.

When povidone species are used, the mass ratio between the content of pemafibrate, a salt thereof or a solvate thereof and the content of the povidone species in the pharmaceutical composition is not particularly limited, and from the viewpoint of improvement of content uniformity, the total content of the povidone species with respect to 1 part by mass of a free form of pemafibrate is preferably 1 to 200 parts by mass, more preferably 3 to 150 parts by mass, particularly preferably 5 to 100 parts by mass.

When linear-chain polymers of 1-vinyl-2-pyrrolidone are used as povidone species, the mass ratio between the content of pemafibrate, a salt thereof or a solvate thereof and the content of the linear-chain polymers of 1-vinyl-2-pyrrolidone is not particularly limited, and from the viewpoint of improvement of content uniformity, the total content of the linear-chain polymers of 1-vinyl-2-pyrrolidone with respect to 1 part by mass of a free form of pemafibrate is preferably 1.5 to 190 parts by mass, more preferably 3.5 to 140 parts by mass, particularly preferably 6 to 90 parts by mass.

When cross-linked polymers of 1-vinyl-2-pyrrolidone are used as povidone species, the mass ratio between the content of pemafibrate, a salt thereof or a solvate thereof and the content of the cross-linked polymers of 1-vinyl-2-pyrroli-done is not particularly limited, and from the viewpoint of improvement of content uniformity, the total content of the cross-linked polymers of 1-vinyl-2-pyrrolidone with respect to 1 part by mass of a free form of pemafibrate is preferably 2 to 180 parts by mass, more preferably 4 to 130 parts by mass, particularly preferably 7 to 80 parts by mass.

<Silicic Acid Compound>

Herein, the "silicic acid compounds" include silicic acid compounds themselves, and salts of silicic acid compounds. Examples of the salts of silicic acid compounds include inorganic salts, and specific examples thereof include alkali metal salts such as sodium salts and potassium salts; salts with metals of Group 2 elements, such as magnesium salts and calcium salts; and salts with metals of Group 13 elements, such as aluminum salts.

Specific examples of the silicic acid compounds include hydrous silicic acid compounds or salts thereof such as hydrated silicon dioxide, amorphous silicon oxide hydrate, hydrous magnesium silicate and hydrous magnesium silicate (natural); anhydrous silicic acids or salts thereof such as light anhydrous silicic acid and heavy anhydrous silicic acid; silicic acids or salts thereof such as silicon dioxide, natural aluminum silicate, synthetic aluminum silicate, synthetic sodium magnesium silicate, calcium silicate, magnesium silicate, aluminum magnesium silicate, magnesium aluminosilicate and magnesium aluminometasilicate; diatomaceous earth; bentonite; kaolin; and talc, and these compounds may be used singly, or in combinations of two or more thereof.

From the viewpoint of improvement of content uniformity, the silicic acid compound is preferably one or more selected from the group consisting of a hydrous silicic acid compound, a salt of a hydrous silicic acid compound, hydrous silicic acid and a salt of hydrous silicic acid, particularly preferably one or more selected from the group consisting of a hydrous silicic acid compound and a salt of a hydrous silicic acid compound.

Among the silicic acid compounds shown as examples, one or more selected from the group consisting of hydrous magnesium silicate, hydrated silicon dioxide and light anhydrous silicic acid are preferable, and one or more selected from the group consisting of hydrous magnesium silicate and hydrated silicon dioxide are more preferable, from the viewpoint of improvement of content uniformity. From the viewpoint of ease of production of a pharmaceutical composition (particularly a solid preparation), the silicic acid compound is preferably solid at normal temperature (any temperature in the range of 15 to 25° C.).

Each of these silicic acid compounds is a known component. The silicic acid compounds may be produced through a known method, or commercially available products may be used. Examples of the commercially available products include Neusilin A (Fuji Chemical Industries Co., Ltd.), FLORITE (Tomita Pharmaceutical Co., Ltd.), Magnesium Silicate (Tomita Pharmaceutical Co., Ltd.), VEEGUMI GRANULE (Sanyo Chemical Industries, Ltd.), VEEGUMI HV GRANULE (Sanyo Chemical Industries, Ltd.), VEEGUMI K GRANULE (Sanyo Chemical Industries, Ltd.), VEEGUMI F (Sanyo Chemical Industries, Ltd.), SYLYSIA 320 (FUJI SILYSIA CHEMICAL LTD.), SYLYSIA 350 (FUJI SILYSIA CHEMICAL LTD.), SYLYSIA 320TP (FUJI SILYSIA CHEMICAL LTD.), SYLYSIA 320FCP (FUJI SILYSIA CHEMICAL LTD.), MICON FR (Tomita Pharmaceutical Co., Ltd.), Silicon Dioxide (NIPPON AEROSIL CO., LTD.), AEROSIL 300 (NIPPON AEROSIL CO., LTD.), Adsolider 101 (Freund Corporation), Adsolider 102 (Freund Corporation), SYLYSIA (FUJI SILYSIA CHEMICAL LTD.), SYLOSPHERE (FUJI SILYSIA CHEMICAL LTD.), Amorphous Silicon Oxide Hydrate (Tosoh Silica Corporation), Neusilin (Fuji Chemical Industries Co., Ltd.), Diatomaceous Earth (Showa Kako Corporation) and Talc (San-Ei Gen F.F.I., Inc.).

When silicic acid compounds are used, the content of the silicic acid compounds in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the silicic acid compounds with respect to the total mass of the pharmaceutical composition is preferably 0.1 to 20 mass %, more preferably 0.5 to 15 mass %, particularly preferably 1 to 10 mass %.

When one or more selected from the group consisting of a hydrous silicic acid compound and a salt thereof are used as silicic acid compounds, the content of one or more selected from the group consisting of a hydrous silicic acid compound and a salt thereof with respect to the total mass of the pharmaceutical composition is preferably 0.2 to 19 mass %, more preferably 0.6 to 14 mass %, particularly preferably 2 to 6 mass %, from the viewpoint of improvement of content uniformity.

When one or more selected from the group consisting of an anhydrous silicic acid compound and a salt thereof are used as silicic acid compounds, the content of one or more selected from the group consisting of am anhydrous silicic acid compound and a salt thereof with respect to the total mass of the pharmaceutical composition is preferably 0.4 to 17 mass %, more preferably 0.8 to 12 mass %, particularly preferably 4 to 8 mass %, from the viewpoint of improvement of content uniformity.

When silicic acid compounds are used, the mass ratio between the content of pemafibrate, a salt thereof or a solvate thereof and the content of the silicic acid compounds in the pharmaceutical composition is not particularly limited, and from the viewpoint of improvement of content uniformity, the total content of the silicic acid compounds with respect to 1 part by mass of a free form of pemafibrate is preferably 1 to 200 parts by mass, more preferably 3 to 150 parts by mass, particularly preferably 5 to 100 parts by mass.

When one or more selected from the group consisting of a hydrous silicic acid compound and a salt thereof are used as silicic acid compounds, the mass ratio between the content of pemafibrate, a salt thereof or a solvate thereof and the content of one or more selected from the group consisting of a hydrous silicic acid compound and a salt thereof is not particularly limited, and from the viewpoint of improvement of content uniformity, the total content of one or more selected from the group consisting of a hydrous silicic acid compound and a salt thereof with respect to 1 part by mass of a free form of pemafibrate is preferably 2 to 160 parts by mass, more preferably 4 to 140 parts by mass, particularly preferably 10 to 90 parts by mass.

When one or more selected from the group consisting of an anhydrous silicic acid compound and a salt thereof are used as silicic acid compounds, the mass ratio between the content of pemafibrate, a salt thereof or a solvate thereof and the content of one or more selected from the group consisting of an anhydrous silicic acid compound and a salt thereof is not particularly limited, and from the viewpoint of improvement of content uniformity, the total content of one or more selected from the group consisting of an anhydrous silicic acid compound and a salt thereof with respect to 1 part by mass of a free form of pemafibrate is preferably 2 to 180 parts by mass, more preferably 4 to 120 parts by mass, particularly preferably 10 to 80 parts by mass.

<Polyhydric Alcohol>

Herein, the "polyhydric alcohol" means compounds having two or more alcoholic hydroxyl groups, other than cellulose ethers having two or more alcoholic hydroxyl groups, disaccharides and cellulose. The polyhydric alcohol may be either a non-polymer or a polymer. Examples of the polyhydric alcohol include sugar alcohols and non-sugar alcohols, and these alcohols may be used singly, or in combinations of two or more thereof. The polyhydric alcohol is preferably a polyhydric alcohol having no cyclic ether structure (for example tetrahydropyran ring) in the molecule or a polyhydric alcohol having only one cyclic ether structure in the molecule, more preferably a polyhydric alcohol having no cyclic ether structure in the molecule, particularly preferably a polyhydric alcohol which is an acyclic compound.

From the viewpoint of ease of production of a pharmaceutical composition (particularly a solid preparation), the polyhydric alcohol is preferably solid at normal temperature (any temperature in the range of 15 to 25° C.).

Specific examples of the sugar alcohol include C3 sugar alcohols (tritols) such as glycerin; C4 sugar alcohols (tetritols) such as erythritol and threitol; C5 sugar alcohols (pentitols) such as xylitol, arabinitol, ribitol and adonitol; C6 sugar alcohols (hexitols) such as mannitol, sorbitol, iditol, dulcitol and galactitol; and C12 sugar alcohols (dodecitols), such as maltitol and lactitol, and these sugar alcohols may be used singly, or in combinations of two or more thereof. For these sugar alcohols, various stereoisomers may be present. The steric configuration of the "sugar alcohol" is not particularly limited, and the "sugar alcohol" may be present as a single stereoisomer, or as a mixture of various stereoisomers at any ratio.

From the viewpoint of improvement of content uniformity, the sugar alcohol is preferably one or more selected from the group consisting of erythritol, xylitol, mannitol, sorbitol, maltitol and lactitol, more preferably one or more selected from the group consisting of mannitol, sorbitol and maltitol, particularly preferably mannitol.

Each of these sugar alcohols is a known component. The sugar alcohols may be produced through a known method, or commercially available products may be used. Examples of the commercially available products include Erythritol (San-Ei Gen F.F.I., Inc.), Xylit (Towa Chemical Industry Co., Ltd.), NEOSORB P (Roquette Japan K.K.), Lesys (Towa Chemical Industry Co., Ltd.), Mannit P (Towa Chemical Industry Co., Ltd.), Glycerin (NOFCORPORATION), MALTISORB (Roquette Japan K.K.) and Amalty Syrup (Towa Chemical Industry Co., Ltd.)

The non-sugar alcohol is preferably a non-sugar alcohol which is an acyclic compound. Specific examples thereof include alkylene glycols such as ethylene glycol, propylene glycol, 1,3-propanediol, 2-methyl-1,3-propanediol and 1,3-butanediol; polyalkylene glycols such as diethylene glycol, dipropylene glycol, macrogol (for example macrogol 100, macrogol 200, macrogol 300, macrogol 400, macrogol 600, macrogol 1000, macrogol 1500, macrogol 1540, macrogol 4000, macrogol 6000, polyethylene glycol 8000, macrogol 20000 and macrogol 35000), polypropylene glycol (for example polypropylene glycol 2000), polyoxyethylene polyoxypropylene glycol (for example polyoxyethylene (3) polyoxypropylene (17) glycol, polyoxyethylene (20) polyoxypropylene (20) glycol, polyoxyethylene (42) polyoxypropylene (67) glycol, polyoxyethylene (54) polyoxypropylene (39) glycol, polyoxyethylene (105) polyoxypropylene (5) glycol, polyoxyethylene (120) polyoxypropylene (40) glycol, polyoxyethylene (124) polyoxypropylene (39) glycol, polyoxyethylene (160) polyoxypropylene (30) glycol, polyoxyethylene (196) polyoxypropylene (67) glycol and polyoxyethylene (200) polyoxypropylene (70) glycol; polyvinyl alcohols such as (fully saponified) polyvinyl alcohol and (partially saponified) polyvinyl alcohol; and meglumine, and these non-sugar alcohols may be used singly, or in combinations of two or more thereof.

From the viewpoint of improvement of content uniformity, the non-sugar alcohol is preferably a dihydric non-sugar alcohol, more preferably a polyalkylene glycol, still more preferably macrogol, yet more preferably one or more selected from the group consisting of macrogol 100, macrogol 200, macrogol 300, macrogol 400, macrogol 600, macrogol 1000, macrogol 1500, macrogol 1540, macrogol 4000, macrogol 6000, polyethylene glycol 8000, macrogol 20000 and macrogol 35000, yet more preferably macrogol having an average molecular weight of 100 to 10,000, yet more preferably macrogol having an average molecular weight of 200 to 8,000, particularly preferably macrogol 6000. The average molecular weight of macrogol can be measured in accordance with "Average molecular mass" described in The Japanese Pharmacopoeia, 17th Edition, Pharmaceutical Preparations, Macrogol 400.

Each of these non-sugar alcohols is a known component. The non-sugar alcohols may be produced through a known method, or commercially available products may be used. Examples of the commercially available products include Kollisolv PG (BASF Japan Ltd.), Diethylene Glycol (Nippon Shokubai Co., Ltd.), UNISAFE DPG-R (NOF CORPORATION), Macrogol 200 (Sanyo Chemical Industries, Ltd.), Kollisolv PEG300 (BASF Japan Ltd.), SUPER REFINED PEG 400 (Croda Japan K.K.), CARBOWAX Sentry PEG 600 (Dow Chemical Japan Limited), Macrogol 1000 (NOF CORPORATION), Macrogol 1500 (Sanyo Chemical Industries, Ltd.), CARBOWAX Sentry PEG 1540 (Dow Chemical Japan Limited), Macrogol 4000 (Sanyo Chemical Industries, Ltd.), Macrogol 6000 (SanyoChemical Industries, Ltd.), Macrogol 20000 (Sanyo Chemical Industries, Ltd.), NEWPOL PP-2000 (Sanyo Chemical Industries, Ltd.), PRONON 101P (NOF CORPORATION), Kollisolv P124 (BASF Japan Ltd.), PRONON 403P (NOF CORPORATION), NEWDET PE-85 (Sanyo Chemical Industries, Ltd.), PEP-101 (Freund Corporation), Kolliphor P188 (BASF Japan Ltd.), Kolliphor P407 Micro (BASF Japan Ltd.) and UNILUBE DP-950B (NOF CORPORATION).

When polyhydric alcohols are used, the content of the polyhydric alcohols in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the polyhydric alcohols with respect to the total mass of the pharmaceutical composition is preferably 0.1 to 99 mass %, more preferably 0.5 to 95 mass %, still more preferably 1 to 90 mass %, particularly preferably 1.5 to 50 mass %.

When sugar alcohols are used as polyhydric alcohols, the content of the sugar alcohols with respect to the total mass of the pharmaceutical composition is preferably 0.2 to 98 mass %, more preferably 0.6 to 94 mass %, particularly preferably 1.1 to 85 mass %, from the viewpoint of improvement of content uniformity.

When non-sugar alcohols are used as polyhydric alcohols, the content of the non-sugar alcohols with respect to the total mass of the pharmaceutical composition is preferably 0.3 to 97 mass, more preferably 0.7 to 93 mass, particularly preferably 1.2 to 80 mass %, from the viewpoint of improvement of content uniformity.

When polyalkylene glycols are used as polyhydric alcohols, the content of the polyalkylene glycols with respect to the total mass of the pharmaceutical composition is preferably 0.4 to 96 mass %, more preferably 0.8 to 92 mass %, particularly preferably 1.3 to 75 mass %, from the viewpoint of improvement of content uniformity.

When polyhydric alcohols are used, the mass ratio between the content of pemafibrate, a salt thereof or a solvate thereof and the content of the polyhydric alcohols in the pharmaceutical composition is not particularly limited, and from the viewpoint of improvement of content uniformity, the total content of the polyhydric alcohols with respect to 1 part by mass of a free form of pemafibrate is preferably 1 to 2,000 parts by mass, more preferably 5 to 1,500 parts by mass, still more preferably 10 to 1,000 parts by mass, particularly preferably 15 to 500 parts by mass.

When sugar alcohols are used as polyhydric alcohols, the mass ratio between the content of pemafibrate, a salt thereof or a solvate thereof and the content of the sugar alcohols in the pharmaceutical composition is not particularly limited, and from the viewpoint of improvement of content uniformity, the total content of the sugar alcohols with respect to 1 part by mass of a free form of pemafibrate is preferably 2 to 1,900 parts by mass, more preferably 6 to 1,450 parts by mass, particularly preferably 12 to 950 parts by mass.

When non-sugar alcohols are used as polyhydric alcohols, the mass ratio between the content of pemafibrate, a salt thereof or a solvate thereof and the content of the non-sugar alcohols in the pharmaceutical composition is not particularly limited, and from the viewpoint of improvement of content uniformity, the total content of the non-sugar alcohols with respect to 1 part by mass of a free form of pemafibrate is preferably 3 to 1,850 parts by mass, more preferably 7 to 1,400 parts by mass, particularly preferably 13 to 900 parts by mass.

When polyalkylene glycols are used as polyhydric alcohols, the mass ratio between the content of pemafibrate, a salt thereof or a solvate thereof and the content of the polyalkylene glycols in the pharmaceutical composition is not particularly limited, and from the viewpoint of improvement of content uniformity, the total content of the polyalkylene glycols with respect to 1 part by mass of a free form of pemafibrate is preferably 4 to 1,800 parts by mass, more preferably 8 to 1,350 parts by mass, particularly preferably 14 to 850 parts by mass.

<Alkyl Sulfate Ester>

Herein, the "alkyl sulfate ester" means an alkyl sulfate ester salt represented by the following formula:

$$R-O-SO_3M \qquad (1)$$

[wherein R represents a linear or branched saturated or unsaturated C8-C22 hydrocarbon group, and M is an alkali metal such as sodium or potassium; a metal of a Group 2 element such as magnesium or calcium; an ammonium ion; or a C2 or C3 hydroxyalkyl-substituted ammonium such as triethanolammonium].

Specific examples of the alkyl sulfate ester include lauryl sulfate ester salts, tetradecyl sulfate ester salts, hexadecyl sulfate ester salts and octadecyl sulfate ester salts, and these sulfate ester salts may be used singly, or in combinations of two or more thereof.

From the viewpoint of improvement of content uniformity, the alkyl sulfate ester is preferably one or more selected from the group consisting of a lauryl sulfate ester salt, a tetradecyl sulfate ester salt, a hexadecyl sulfate ester salt and an octadecyl sulfate ester salt, more preferably a lauryl sulfate ester salt, particularly preferably sodium lauryl sulfate. From the viewpoint of ease of production of a pharmaceutical composition (particularly a solid preparation), the alkyl sulfate ester is preferably solid at normal temperature (any temperature in the range of 15 to 25° C.).

Each of these alkyl sulfate esters is a known component. The alkyl sulfate esters may be produced through a known method, or commercially available products may be used. Examples of the commercially available products include Kolliphor SLS (BASF Japan Ltd.).

When alkyl sulfate esters are used, the content of the alkyl sulfate esters in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the alkyl esters with respect to the total mass of the pharmaceutical composition is preferably 0.1 to 20 mass %, more preferably 0.5 to 15 mass %, particularly preferably 1 to 10 mass %.

When alkyl sulfate esters are used, the mass ratio between the content of pemafibrate, a salt thereof or a solvate thereof and the content of the alkyl sulfate esters in the pharmaceutical composition is not particularly limited, and from the viewpoint of improvement of content uniformity, the total content of the alkyl sulfate esters with respect to 1 part by mass of a free form of pemafibrate is preferably 1 to 200 parts by mass, more preferably 3 to 150 parts by mass, still more preferably 5 to 100 parts by mass, particularly preferably 5 to 50 parts by mass.

<Disaccharide Species>

Herein, the "disaccharide species" means one or more selected from the group consisting of a disaccharide itself; a disaccharide in which all or some of hydroxy groups are substituted with halogen atoms such as chlorine atoms; and a solvate thereof. Here, the solvate is not particularly limited, and specific examples thereof include hydrates. The type of monosaccharide forming the disaccharide is not particularly limited, and examples thereof include pentoses such as arabinose and xylose; and hexoses such as glucose, galactose, fructose, mannose, altrose and rhamnose.

Specific examples of the disaccharide species include sucrose (cane sugar), lactulose, lactose (milk sugar), maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, primevelose and sucralose, and these disaccharides may be used singly, or in combinations of two or more thereof.

From the viewpoint of improvement of content uniformity, the disaccharide species is preferably one or more selected from the group consisting of sucrose, lactose, maltose, trehalose, palatinose, sucralose and a solvate thereof, more preferably one or more selected from the group consisting of sucrose, lactose, trehalose, sucralose-anda hydrate thereof, still more preferably one or more selected from the group consisting of lactose and a hydrate thereof, particularly preferably one or more selected from the group consisting of a lactose/microcrystalline cellulose spherical grain, a lactose monohydrate, a lactose granularized product and an anhydrous lactose. From the viewpoint of ease of production of a pharmaceutical composition (particularly a solid preparation), the disaccharide species is preferably solid at normal temperature (any temperature in the range of 15 to 25° C.).

Each of these disaccharide species is a known component. The disaccharide species may be produced through a known method, or commercially available products may be used. Examples of the commercially available products include NONPAREIL-105 (Freund Corporation), Lactose monohydrate (San-Ei Gen F.F.I., Inc.), Lactose G (Freund Corporation), Lactopress anhydrous (CBC Co., Ltd.), Nishoku Crystalline Maltose (Nihon Shokuhin Kako Co., Ltd.), Trehalose P (Asahi Kasei Corporation), Sucralose (San-Ei Gen F.F.I., Inc.) and Pharmatose 200M (DFE pharma).

When disaccharide species are used, the content of the disaccharide species in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the disaccharide species with respect to the total mass of the pharmaceutical composition is preferably 1 to 99 mass %, more preferably 3 to 95 mass %, still more preferably 5 to 90 mass %, particularly preferably 7 to 85 mass %.

When one or more selected from the group consisting of lactose and a hydrate thereof are used as disaccharide species, the content thereof with respect to the total mass of the pharmaceutical composition is preferably 2 to 98 mass %, more preferably 4 to 93 mass %, particularly preferably 8 to 80 mass %, from the viewpoint of improvement of content uniformity.

When disaccharide species are used, the mass ratio between the content of pemafibrate, a salt thereof or a solvate thereof and the content of the disaccharide species in the pharmaceutical composition is not particularly limited, and from the viewpoint of improvement of content uniformity, the total content of the disaccharide species with respect to 1 part by mass of a free form of pemafibrate is preferably 10 to 1,750 parts by mass, more preferably 50 to 1,500 parts by mass, still more preferably 80 to 1,200 parts by mass, particularly preferably 100 to 900 parts by mass.

When one or more selected from the group consisting of lactose and a hydrate thereof are used as disaccharide species, the mass ratio between the content of pemafibrate, a salt thereof or a solvate thereof and the content of one or more selected from the group consisting of lactose and a hydrate thereof in the pharmaceutical composition is not particularly limited, and from the viewpoint of improvement of content uniformity, the total content of one or more selected from the group consisting of lactose and a hydrate thereof with respect to 1 part by mass of a free form of pemafibrate is preferably 30 to 1,150 parts by mass, more preferably 50 to 1,050 parts by mass, still more preferably 70 to 950 parts by mass, particularly preferably 120 to 850 parts by mass.

<Cellulose>

Herein, the "cellulose" means one or more selected from the group consisting of cellulose and a salt thereof. In the cellulose, the salt is not particularly limited, and specific examples thereof include alkali metal salts such as sodium salts and potassium salts; and salts with metals of Group 2 elements, such as calcium salts and magnesium salts. The average degree of polymerization, the form (crystal form) and the like of the cellulose are not particularly limited, and the average degree of polymerization is preferably 50 to 10,000. Here, the average degree of polymerization can be determined by conducting a test in accordance with Identification (3) described in The Japanese Pharmacopoeia, 17th Edition, "Microcrystalline Cellulose".

Specific examples of the cellulose include crystalline cellulose, crystalline cellulose (fine particles), crystalline cellulose (grain), powdered cellulose and powdered cellulose (average degree of polymerization: 800 to 1,100), and these celluloses may be used singly, or in combinations of two or more thereof. The crystalline cellulose and the like are the microcrystalline cellulose and the like described in Japanese Pharmaceutical Excipients Directory 2016 (issued by Yakuji Nippo, Limited).

Each of these celluloses is a known component. The celluloses may be produced through a known method, or commercially available products may be used. Examples of the commercially available products include CEOLUS PH-101 (Asahi Kasei Corporation), CELPHERE (San-Ei Gen F.F.I., Inc.) and ARBOCEL (Kimura Sangyo Co., Ltd.).

When cellulose is used, the content of the cellulose in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the cellulose with respect to the total mass of the pharmaceutical composition is preferably 1 to 40 mass %, more preferably 3 to 35 mass %, still more preferably 5 to 30 mass %, particularly preferably 8 to 25 mass %.

When cellulose is used, the mass ratio between the content of pemafibrate, a salt thereof or a solvate thereof and the content of the cellulose in the pharmaceutical composition is not particularly limited, and from the viewpoint of improvement of content uniformity, the total content of the cellulose with respect to 1 part by mass of a free form of pemafibrate is preferably 5 to 5,000 parts by mass, more preferably 30 to 3,500 parts by mass, particularly preferably 60 to 2,000 parts by mass.

Herein, the dosage form of the "pharmaceutical composition" is not particularly limited, may be a solid, semisolid or liquid preparation, and can be selected according to the use purpose of the pharmaceutical composition. Examples of the dosage form of the pharmaceutical composition include dosage forms described in The Japanese Pharmacopoeia, 17th Edition, General Rules for Preparations. Specific examples of the peroral dosage form include solid preparations such as tablets (e.g. normal tablets, orally disintegrating tablets, chewable tablets, effervescent tablets, dispersion tablets and soluble tablets), capsules, granules (e.g. effervescent granules), powders and pills; semisolid preparations such as peroral jellies; liquid preparations such as peroral liquids (e.g. elixirs, suspensions, emulsions and lemonades). Examples of the parenteral dosage form include injections, inhalations, eye drops, ear drops, nasal drops, suppositories, solid external preparations, liquid external preparations, sprays, ointments, creams, gels and patches.

The pharmaceutical composition is preferably a solid preparation from the viewpoint of ease of administration and ease of production. In particular, when the pharmaceutical composition is a solid preparation, production is very easy, but since in general, a solid preparation is produced basically with solid components used in a large amount at normal temperature (any temperature in the range of 15 to 25° C.), components are apt to be unevenly mixed and dispersed, so that deterioration in content uniformity is apt to be particularly problematic. On the other hand, the present invention exhibits the following excellent advantage: even a solid preparation has good content uniformity.

The solid preparation is preferably a peroral solid preparation, more preferably a tablet, a capsule, a granule, a powder or a pill, particularly preferably a tablet.

In addition to the above-described components, pharmaceutically acceptable carriers (preparation additives) may be added to the pharmaceutical composition of the present invention depending on its dosage form. Examples of the preparation additives include, but are not limited to, diluents, disintegrants, binders, lubricants, plasticizers, film formers, powders, poorly water-soluble polymer substances, antioxidants, flavors and sweetening agents. As specific examples of these preparation additives, those described in Japanese Pharmaceutical Excipients Directory 2016 (issued by Yakuji Nippo, Limited), Handbook of Pharmaceutical Excipients, Seventh Edition (issued by Pharmaceutical Press), etc. may be used.

Specific examples of the diluents include inorganic diluents such as anhydrous sodium sulfate, anhydrous dibasic calcium phosphate, sodium chloride, calcium sulfate, calcium phosphate monobasic, dibasic calcium phosphate, dibasic sodium phosphate, monobasic potassium phosphate, monobasic calcium phosphate and monobasic sodium phosphate; and organic diluents such as caramel, agar, paraffin, glucose, pullulan, polyoxyethylene hardened castor oil, aminoalkyl methacrylate copolymers E, polyvinylacetal diethylaminoacetate and calcium citrate. These diluents may be used singly, or in combinations of two or more thereof.

The total content of the diluents is not particularly limited, and preferably 20 to 99 mass %, more preferably 30 to 97 mass %, with respect to the total mass of the pharmaceutical composition.

Specific examples of the disintegrants include gelatin, sodium hydrogen carbonate, dextrin, dehydroacetic acid and salts thereof and polyoxyethylene hardened castor oil 60. These disintegrants may be used singly, or in combinations of two or more thereof.

Specific examples of the binders include dextrin, pullulan, acacia, agar, gelatin, tragacanth, sodium alginate, aminoalkyl methacrylate copolymers E and polyvinylacetal diethylaminoacetate. These binders may be used singly, or in combinations of two or more thereof.

Specific examples of the lubricants include calcium stearate, magnesium stearate and sodium stearyl fumarate. Theses lubricants may be used singly, or in combinations of two or more thereof.

The total content of the lubricants is not particularly limited, and preferably 0.01 to 15 mass %, more preferably 0.1 to 10 mass %, with respect to the total mass of the pharmaceutical composition.

Specific examples of the plasticizers include sesame oil, castor oil and polysorbate 80 (polyoxyethylene (20) sorbitan oleate ester). These plasticizers may be used singly, or in combinations of two or more thereof.

Specific examples of the film formers include alginic acid or salts thereof such as sodium alginate, carrageenan, xanthan gum and pullulan. These film formers may be used singly, or in combinations of two or more thereof.

Specific examples of the powders include organic and inorganic powders such as powders of talc, titanium oxide, yellow ferric oxide, red ferric oxide and legal color pigments. These powders may be used singly, or in combinations of two or more thereof.

Specific examples of the poorly water-soluble polymer substances include carboxyvinyl polymers and aminoalkyl methacrylate copolymers. These substances may be used singly, or in combinations of two or more thereof.

Specific examples of the antioxidants include ascorbic acid, sodium hydrogen sulfite, sodium sulfite, sodium edetate, erythorbic acid, tocopherol acetate, dibutylhydroxytoluene, natural vitamin E, tocopherol and butylhydroxyanisole. These antioxidants may be used singly, or in combinations of two or more thereof.

Specific examples of the flavors include terpenes such as limonene, pinene, camphene, cymene, cineole, citronellol, geraniol, nerol, linalool, menthol, terpineol, rhodinol, borneol, isoborneol, menthone, camphor, eugenol and cinnzeylanol; terpene-containing essential oils such as bitter orange oil, orange oil, peppermint oil, camphor white oil, *eucalyptus* oil, turpentine oil, lemon oil, ginger oil, clove oil, cinnamon oil, lavender oil, fennel oil, chamomile oil, fermented soybean oil and spearmint oil; and sour flavors such as ascorbic acid, tartaric acid, citric acid, malic acid and salts thereof. These flavors may be used singly, or in combinations of two or more thereof.

Examples of the sweetening agents include aspartame, *stevia*, glycyrrhizic acid, thaumatin, acesulfame potassium, saccharin and saccharin sodium, and these sweetening agents may be used singly, or in combinations of two or more thereof.

The pharmaceutical composition of the present invention can be produced through a known method depending on its dosage form.

For example, the pharmaceutical composition, when it is a solid preparation, can be produced through appropriate combination of unit operations such as grinding, mixing, granulation, drying, grain size adjustment, classification, filling, palletizing and coating.

More specifically, for example, when the dosage form of the pharmaceutical composition is a granular preparation such as a granule, a powder or a pill, the components 1 to 8 and preparation additives such as diluents, binders, disintegrants and lubricants are mixed in accordance with needs, the mixture is then granulated through a known granulation method such as extrusion granulation, tumbling granulation, agitation granulation, fluidized bed granulation, spray granulation, melt granulation or crushing granulation to obtain a granulated product, and the granulated product is subjected to classification, grain size adjustment and the like in accordance with needs, whereby the pharmaceutical composition can be produced. The obtained granulated product can be coated through a known method with a coating agent etc.

When the dosage form of the pharmaceutical composition is a tablet, the components 1 to 8 and appropriate preparation additives such as diluents, binders, disintegrants and lubricants are mixed in accordance with needs to obtain a mixture, and the mixture is directly compressed (pelletized) (through a direct powder compression method), or compressed (pelletized) (through a semidry grain compression method, dry granule compression method, wet grain compression method or the like) after the above-described granulated product is subjected to classification, grain size adjustment and the like, whereby the pharmaceutical composition can be produced. The obtained compressed product (tablet) can be coated through a known method with a coating agent etc.

When the dosage form of the pharmaceutical composition is a capsule, the granulated product or compressed product may be capsulated.

The disease to which the pharmaceutical composition of the present invention is applied is not limited, and the pharmaceutical composition can be widely used for prevention or treatment of diseases against which administration of pemafibrate is known or expected to be effective.

For example, pemafibrate, a salt thereof or a solvate thereof has excellent PPAR-α agonist activity, and exhibits plasma triglyceride concentration reducing action, HDL cholesterol increasing action, etc. Therefore, the pharmaceutical composition of the present invention can be used preferably as a drug for prevention and/or treatment of dyslipidemia (hyperlipidemia, more specifically, for example primary hyperlipidemia and secondary hyperlipidemia), further preferably as a drug for prevention and/or treatment of hypertriglyceridemia, etc.

In addition, pemafibrate, a salt thereof or a solvate thereof is useful for prevention or treatment of NAFLD (non-alcoholic fatty liver disease). Therefore, the pharmaceutical composition of the present invention can also be used as a drug for prevention and/or treatment of NAFLD (more preferably NASH (non-alcoholic steatohepatitis)), etc.

Further, pemafibrate, a salt thereof or a solvate thereof may be used as a drug for treatment of primary biliary cirrhosis, etc.

The administration route of the pharmaceutical composition is not particularly limited, and can be determined in appropriate consideration of the target disease, the type of preparation, the sex, age, symptoms of a patient in need of the composition, and the like, but peroral administration is preferable from the viewpoint of ease of administration. The daily dose of the pharmaceutical composition can be taken as a single dose, or can be divided into 2 to 4 daily administrations, and taken before each meal, between meals, after each meal, before bedtime, or the like.

The dose of pemafibrate, a salt thereof or a solvate thereof in the pharmaceutical composition is not particularly limited, and can be determined in appropriate consideration of the target disease, the type of preparation, the sex, age, symptoms of a patient in need of the composition, and the like. For example, the daily dose of pemafibrate, a salt thereof or a solvate thereof may be 0.05 to 0.8 mg, more preferably 0.075 to 0.6 mg, particularly preferably 0.1 to 0.4 mg, in terms of a free form of pemafibrate.

The following aspects are disclosed herein as examples, which should not be construed as limiting the present invention thereto.

[1-1] A pharmaceutical composition comprising pemafibrate, a salt thereof or a solvate thereof in an amount of 0.017 to 4.2 mass % (preferably 0.042 to 4.2 mass %, more preferably 0.042 to 1.7 mass %, particularly preferably 0.042 to 0.83 mass %) in terms of a free form of pemafibrate with respect to the total mass of the pharmaceutical composition.

[1-2] The pharmaceutical composition described in [1-1], comprising pemafibrate, a salt thereof or a solvate thereof in an amount of 0.02 to 5 mg (preferably 0.05 to 1 mg) in terms of a free form of pemafibrate per unit dose of the pharmaceutical composition.

[1-3] The pharmaceutical composition described in [1-1] or [1-2], wherein the pharmaceutical composition is a solid preparation.

[1-4] The pharmaceutical composition described in any of [1-1] to [1-3], wherein the dosage form thereof is a tablet, a capsule, a granule, a powder or a pill.

[1-5] The pharmaceutical composition described in any of [1-1] to [1-4], comprising pemafibrate, a salt thereof or a solvate thereof in an amount of 0.02 to 5 mg (preferably 0.05 to 1 mg) in terms of a free form of pemafibrate per tablet.

[1-6] The pharmaceutical composition described in any of [1-1] to [1-5], further comprising one or more selected from the group consisting of the following components (1) to (8):
(1) cellulose ether species;
(2) starch species;
(3) povidone species;
(4) silicic acid compound;
(5) polyhydric alcohol;
(6) alkyl sulfate ester;
(7) disaccharide species; and
(8) cellulose.

[1-7] The pharmaceutical composition described in [1-6], wherein component (1) is one or more selected from the group consisting of an alkylcellulose, a hydroxyalkylcellulose, an alkyl(hydroxyalkyl)cellulose, a carboxyalkylcellulose, a cross-linked polymer of a carboxyalkylcellulose and a salt thereof.

[1-8] The pharmaceutical composition described in [1-6], wherein component (1) is one or more selected from the group consisting of a C1-C6 alkylcellulose, a hydroxy C1-C6 alkylcellulose, a C1-C6 alkyl(hydroxy C1-C6 alkyl)cellulose, a carboxy C1-C6 alkylcellulose, a cross-linked polymer of a carboxy C1-C6 alkylcellulose and a salt thereof.

[1-9] The pharmaceutical composition described in [1-6], wherein component (1) is one or more selected from the group consisting of methylcellulose, ethylcellulose, hydroxypropylcellulose, hypromellose, carmellose, carmellose potassium, carmellose calcium, carmellose sodium and croscarmellose sodium.

[1-10] The pharmaceutical composition described in any one of [1-6] to [1-9], wherein component (2) is one or more selected from the group consisting of starch, a hydroxyalkyl ether of starch, a carboxyalkyl ether of starch and a salt thereof.

[1-11] The pharmaceutical composition described in any one of [1-6] to [1-9], wherein component (2) is one or more selected from the group consisting of starch, a hydroxy C1-C6 alkyl ether of starch, a carboxy C1-C6 alkyl ether of starch and a salt thereof.

[1-12] The pharmaceutical composition described in any one of [1-6] to [1-9], wherein component (2) is one or more selected from the group consisting of starch, hydroxypropyl starch, carboxymethyl starch and a salt thereof.

[1-13] The pharmaceutical composition described in any one of [1-6] to [1-12], wherein component (3) is one or more selected from the group consisting of povidone and crospovidone.

[1-14] The pharmaceutical composition described in any one of [1-6] to [1-12], wherein component (3) is crospovidone.

[1-15] The pharmaceutical composition described in any one of [1-6] to [1-14], wherein component (4) is one or more selected from the group consisting of a hydrous silicic acid compound, a salt of a hydrous silicic acid compound, anhydrous silicic acid and a salt of anhydrous silicic acid.

[1-16] The pharmaceutical composition described in any one of [1-6] to [1-14], wherein component (4) is one or more selected from the group consisting of hydrous magnesium silicate, hydrated silicon dioxide and light anhydrous silicic acid.

[1-17] The pharmaceutical composition described in any one of [1-6] to [1-14], wherein component (4) is one or more selected from the group consisting of hydrous magnesium silicate and hydrated silicon dioxide.

[1-18] The pharmaceutical composition described in any one of [1-6] to [1-17], wherein component (5) is macrogol.

[1-19] The pharmaceutical composition described in any one of [1-6] to [1-17], wherein component (5) is one or more selected from the group consisting of macrogol 100, macrogol 200, macrogol 300, macrogol 400, macrogol 600, macrogol 1000, macrogol 1500, macrogol 1540, macrogol 4000, macrogol 6000, polyethylene glycol 8000, macrogol 20000 and macrogol 35000.

[1-20] The pharmaceutical composition described in any one of [1-6] to [1-17], wherein component (5) is macrogol having an average molecular weight of 100 to 10,000.

[1-21] The pharmaceutical composition described in any one of [1-6] to [1-17], wherein component (5) is macrogol 6000.

[1-22] The pharmaceutical composition described in any one of [1-6] to [1-17], wherein component (5) is one or more selected from the group consisting of erythritol, xylitol, mannitol, sorbitol, maltitol and lactitol.

[1-23] The pharmaceutical composition described in any one of [1-6] to [1-17], wherein component (5) is one or more selected from the group consisting of mannitol and sorbitol.

[1-24] The pharmaceutical composition described in any one of [1-6] to [1-17], wherein component (5) is mannitol.

[1-25] The pharmaceutical composition described in any one of [1-6] to [1-24], wherein component (6) is one or more selected from the group consisting of a lauryl sulfate ester salt, a tetradecyl sulfate ester salt, a hexadecyl sulfate ester salt and an octadecyl sulfate ester salt.

[1-26] The pharmaceutical composition described in any one of [1-6] to [1-24], wherein component (6) is a lauryl sulfate ester salt.

[1-27] The pharmaceutical composition described in any one of [1-6] to [1-24], wherein component (6) is sodium-lauryl sulfate.

[1-28] The pharmaceutical composition described in any one of [1-6] to [1-27], wherein component (7) is one or more selected from the group consisting of sucrose (cane sugar), lactulose, lactose (milk sugar), maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, primevelose, sucralose and a solvate thereof.

[1-29] The pharmaceutical composition described in any one of [1-6] to [1-27], wherein component (7) is one or more selected from the group consisting of sucrose, lactose, maltose, trehalose, palatinose, sucralose and a solvate thereof.

[1-30] The pharmaceutical composition described in any one of [1-6] to [1-27], wherein component (7) is one or more selected from the group consisting of sucrose, lactose, trehalose, sucralose and a solvate thereof.

[1-31] The pharmaceutical composition described in any one of [1-6] to [1-27], wherein component (7) is one or more selected from the group consisting of lactose and a hydrate thereof.

[1-32] The pharmaceutical composition described in any one of [1-6] to [1-31], wherein component (8) is one or more selected from the group consisting of cellulose and a salt thereof.

[1-33] The pharmaceutical composition described in any one of [1-1] to [1-32], wherein the pharmaceutical composition is a drug for prevention and/or treatment of a disease selected from dyslipidemia (hyperlipidemia), more specifically, for example primary hyperlipidemia and secondary hyperlipidemia), NAFLD (more preferably NASH (non-alcoholic steatohepatitis)) and primary biliary cirrhosis.

[2-1] A method for improving the content uniformity of pemafibrate, a salt thereof or a solvate thereof in a pharmaceutical composition, the method comprising the step of incorporating pemafibrate, a salt thereof or a solvate thereof in an amount of 0.017 to 4.2 mass % (preferably 0.042 to 4.2 mass %, more preferably 0.042 to 1.7 mass %, particularly preferably 0.042 to 0.83 mass %) in terms of a free form of pemafibrate with respect to the total mass of the pharmaceutical composition (preferably, a method for improving the content uniformity of pemafibrate, a salt thereof or a solvate thereof in a pharmaceutical composition, the method comprising setting the content of pemafibrate, a salt thereof or a solvate thereof in the pharmaceutical composition to 0.017 to 4.2 mass % (preferably 0.042 to 4.2 mass %, more preferably 0.042 to 1.7 mass %, particularly preferably 0.042 to 0.83 mass %) in terms of a free form of pemafibrate with respect to the total mass of the pharmaceutical composition).

[2-2] The method described in [2-1], wherein the step is a step of incorporating pemafibrate, a salt thereof or a solvate thereof in an amount of 0.02 to 5 mg (preferably 0.05 to 1 mg) in terms of a free form of pemafibrate per unit dose of the pharmaceutical composition.

[2-3] The method described in [2-1] or [2-2], wherein the pharmaceutical composition is a solid preparation.

[2-4] The method described in any of [2-1] to [2-3], wherein the dosage form of the pharmaceutical composition is a tablet, a capsule, a granule, a powder or a pill.

[2-5] The method described in any of [2-1] to [2-4], wherein the step is a step of incorporating pemafibrate, a salt thereof or a solvate thereof in an amount of 0.02 to 5 mg (preferably 0.05 to 1 mg) in terms of a free form of pemafibrate per tablet.

[2-6] The method described in any of [2-1] to [2-5], comprising the step of incorporating one or more selected from the following components (1) to (8):
(1) cellulose ether species;
(2) starch species;
(3) povidone species;
(4) silicic acid compound;
(5) polyhydric alcohol;
(6) alkyl sulfate ester;
(7) disaccharide species; and
(8) cellulose,
in a pharmaceutical composition.

[2-7] The method described in [2-6], wherein component (1) is one or more selected from the group consisting of an alkylcellulose, a hydroxyalkylcellulose, an alkyl(hydroxyalkyl)cellulose, a carboxyalkylcellulose, a cross-linked polymer of a carboxyalkylcellulose and a salt thereof.

[2-8] The method described in [2-6], wherein component (1) is one or more selected from the group consisting of a C1-C6 alkylcellulose, a hydroxy C1-C6 alkylcellulose, a C1-C6 alkyl(hydroxy C1-C6 alkyl)cellulose, a carboxy C1-C6 alkylcellulose, a cross-linked polymer of a carboxy C1-C6 alkylcellulose and a salt thereof.

[2-9] The method described in [2-6], wherein component (1) is one or more selected from the group consisting of methylcellulose, ethylcellulose, hydroxypropylcellulose, hypromellose, carmellose, carmellose potassium, carmellose calcium, carmellose sodium and croscarmellose sodium.

[2-10] The method described in any one of [2-6] to [2-9], wherein component (2) is one or more selected from the group consisting of starch, a hydroxyalkyl ether of starch, a carboxyalkyl ether of starch and a salt thereof.

[2-11] The method described in any one of [2-6] to [2-9], wherein component (2) is one or more selected from the group consisting of starch, a hydroxy C1-C6 alkyl ether of starch, a carboxy C1-C6 alkyl ether and a salt thereof.

[2-12] The method described in any one of [2-6] to [2-9], wherein component (2) is one or more selected from the group consisting of starch, hydroxypropyl starch, carboxymethyl starch and a salt thereof.

[2-13] The method described in any one of [2-6] to [2-12], wherein component (3) is one or more selected from the group consisting of povidone and crospovidone.

[2-14] The method described in anyone of [2-6] to [2-12], wherein component (3) is crospovidone.

[2-15] The method described in anyone of [2-6] to [2-14], wherein component (4) is one or more selected from the group consisting of a hydrous silicic acid compound, a salt of a hydrous silicic acid compound, anhydrous silicic acid and a salt of anhydrous silicic acid.

[2-16] The method described in anyone of [2-6] to [2-14], wherein component (4) is one or more selected from the group consisting of hydrous magnesium silicate, hydrated silicon dioxide and light anhydrous silicic acid.

[2-17] The method described in anyone of [2-6] to [2-14], wherein component (4) is one or more selected from the group consisting of hydrous magnesium silicate and hydrated silicon dioxide.

[2-18] The method described in anyone of [2-6] to [2-17], wherein component (5) is macrogol.

[2-19] The method described in anyone of [2-6] to [2-17], wherein component (5) is one or more selected from the group consisting of macrogol 100, macrogol 200, macrogol 300, macrogol 400, macrogol 600, macrogol 1000, macrogol 1500, macrogol 1540, macrogol 4000, macrogol 6000, polyethylene glycol 8000, macrogol 20000 and macrogol 35000.

[2-20] The method described in any one of [2-6] to [2-17], wherein component (5) is macrogol having an average molecular weight of 100 to 10,000.

[2-21] The method described in anyone of [2-6] to [2-17], wherein component (5) is macrogol 6000.

[2-22] The method described in anyone of [2-6] to [2-17], wherein component (5) is one or more selected from the group consisting of erythritol, xylitol, mannitol, sorbitol, maltitol and lactitol.

[2-23] The method described in any one of [2-6] to [2-17], wherein component (5) is one or more selected from the group consisting of mannitol and sorbitol.

[2-24] The method described in any one of [2-6] to [2-17], wherein component (5) is mannitol.

[2-25] The method described in anyone of [2-6] to [2-24], wherein component (6) is one or more selected from the group consisting of a lauryl sulfate ester salt, a tetradecyl sulfate ester salt, a hexadecyl sulfate ester salt and an octadecyl sulfate ester salt.

[2-26] The method described in anyone of [2-6] to [2-24], wherein component (6) is a lauryl sulfate ester salt.

[2-27] The method described in anyone of [2-6] to [2-24], wherein component (6) is sodium lauryl sulfate.

[2-28] The method described in anyone of [2-6] to [2-27], wherein component (7) is one or more selected from the group consisting of sucrose (cane sugar), lactulose, lactose (milk sugar), maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, primevelose, sucralose and a solvate thereof.

[2-29] The method described in any one of [2-6] to [2-27], wherein component (7) is one or more selected from the group consisting of sucrose, lactose, maltose, trehalose, palatinose, sucralose and a solvate thereof.

[2-30] The method described in any one of [2-6] to [2-27], wherein component (7) is one or more selected from the group consisting of sucrose, lactose, trehalose, sucralose and a solvate thereof.

[2-31] The method described in any one of [2-6] to [2-27], wherein component (7) is one or more selected from the group consisting of lactose and a hydrate thereof.

[2-32] The method described in any one of [2-6] to [2-31], wherein component (8) is one or more selected from the group consisting of cellulose and a salt thereof.

[2-33] The method described in anyone of [2-1] to [2-32], wherein the pharmaceutical composition is a drug for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

EXAMPLES

The present invention will next be described in detail by way of Examples, which should not be construed as limiting the invention thereto.

In Test Examples below, measurement was performed through HPLC using an ODS column as a column and an ultraviolet spectrophotometer as a detector.

For pemafibrate used in Test Examples below, the average particle diameters of primary particles were measured in accordance with The Japanese Pharmacopoeia, 17th Edition, Laser Diffraction Measurement of Particle Size, and the results showed that the d50 value was 100 µm or less, and the d90 value was 200 µm or less.

Test Example 1

Content Uniformity Evaluation Test (1)

The following test was conducted for evaluating the uniformity of the content of pemafibrate in a pharmaceutical composition.

The tablets of Examples 1 to 8 were produced using the components shown in Table 1 in such a manner that the amounts (mg) of the components per tablet were as shown in Table 1.

Pemafibrate and croscarmellose sodium were mixed for 30 seconds, lactose monohydrate and microcrystalline cellulose were added, the mixture was mixed for 30 seconds, magnesium stearate was added, and the mixture was mixed for 30 seconds. Thereafter, using a tablet press equipped with a punch having a diameter of 7 mm, the resulting mixture was pelletized to obtain 1,000 tablets each having a weight of 120 mg.

From the obtained tablets, ten tablets were randomly picked up, and the content of pemafibrate in each tablet was measured through the following method.

One tablet was put in water to crush the tablet, and acetonitrile was then added to obtain a sample solution. The obtained sample solution was analyzed with a HPLC apparatus to measure the pemafibrate-derived peak area. By comparing the pemafibrate-derived peak area for the obtained sample solution to the peak area for a standard solution of pemafibrate with a known concentration, the pemafibrate content per tablet was measured.

From the thus-obtained measured value of the pemafibrate content per tablet, a relative standard deviation (RSD) (%) of the pemafibrate content in the tablet was calculated in accordance with The Japanese Pharmacopoeia, 17th Edition, Content Uniformity Test, and used as an index of variation (degree of uniformity) of the pemafibrate content in the tablet.

Table 1 shows the results.

TABLE 1

| Components | Amount blended (mg) (per tablet) | | | | | | | |
| --- | --- | --- | --- | --- | --- | --- | --- | --- |
| | Example 1 | Example 2 | Example 3 | Example 4 | Example 5 | Example 6 | Example 7 | Example 8 |
| Pemafibrate | 0.01 | 0.02 | 0.05 | 0.1 | 0.5 | 1.0 | 5.0 | 10.0 |
| Lactose monohydrate | q.s. | q.s. | q.s. | q.s. | q.s. | q.s. | q.s. | q.s. |
| Microcrystalline cellulose | 24 | 24 | 24 | 24 | 24 | 24 | 24 | 24 |
| Croscarmellose sodium | 2.4 | 2.4 | 2.4 | 2.4 | 2.4 | 2.4 | 2.4 | 2.4 |
| Magnesium stearate | 1.2 | 1.2 | 1.2 | 1.2 | 1.2 | 1.2 | 1.2 | 1.2 |
| Total | 120 | 120 | 120 | 120 | 120 | 120 | 120 | 120 |
| Pemafibrate content (ratio with respect to total mass of pharmaceutical composition: content in terms of a free form pemafibrate) (mass %) | 0.0083 | 0.017 | 0.042 | 0.083 | 0.42 | 0.83 | 4.2 | 8.3 |
| Relative standard deviation (RSD) (%) | 14.4 | 6.1 | 3.8 | 2.7 | 3.7 | 2.0 | 5.2 | 8.2 |

The amount blended (mg) and the content (mass %) of pemafibrate in the table are values calculated from the amount added.

As is apparent from the results shown in Table 1, the tablets having a pemafibrate content of less than 0.017 mass % (Example 1) and a pemafibrate content of more than 4.2 mass % (Example 8) all had a high relative standard deviation of more than 8%, and poor uniformity of the content of pemafibrate per tablet.

In contrast, the tablets having a pemafibrate content of 0.017 to 4.2 mass % (Examples 2 to 7) all had a relative standard deviation of less than 8%, and good uniformity of the content pemafibrate per tablet.

The above test results reveal that in a pharmaceutical composition containing pemafibrate, a salt thereof or a solvate thereof, by setting the content of pemafibrate, a salt thereof or a solvate thereof within the range of 0.017 to 4.2 mass % in terms of a free form of pemafibrate with respect to the total mass of the pharmaceutical composition, the content uniformity of pemafibrate in the pharmaceutical composition is improved.

Test Example 2

Content Uniformity Evaluation Test (2)

The following test was conducted for evaluating the uniformity of the content of pemafibrate in a pharmaceutical composition.

The tablets of Examples 9 to 12 were produced using the components shown in Table 2 in such a manner that the amounts (mg) of the components per tablet were as shown in Table 2.

Pemafibrate and cellulose ether species were mixed for 30 seconds, lactose monohydrate and microcrystalline cellulose were added, the mixture was mixed for 30 seconds, magnesium stearate was added, and the mixture was mixed for 30 seconds. Thereafter, using a tablet press equipped with a punch having a diameter of 7 mm, the resulting mixture was pelletized to obtain 1,000 tablets each having a weight of 120 mg.

From the obtained tablets, ten tablets were randomly picked up, and the content of pemafibrate in each tablet was measured through the same method as in Test Example 1. From the thus-obtained measured value of the pemafibrate content per tablet, a relative standard deviation (RSD) (%) of the pemafibrate content in the tablet was calculated in accordance with The Japanese Pharmacopoeia, 17th Edition, Content Uniformity Test, and used as an index of variation (degree of uniformity) of the pemafibrate content in the tablet.

Table 2 shows the results.

The above test results reveal that pharmaceutical compositions containing 0.017 to 4.2 mass % of pemafibrate, a salt thereof or a solvate thereof and cellulose ether species have good content uniformity.

Test Example 3

Content uniformity evaluation test (3) A test was conducted through the same method as in Test Example 2 except that tablets had compositions in which components and the amounts thereof were as shown in Table 3 below.

Table 3 shows the results.

TABLE 3

| | | Amount blended (mg) (per tablet) | | |
|---|---|---|---|---|
| Components | | Example 13 | Example 14 | Example 15 |
| Pemafibrate | | 0.1 | 0.1 | 0.1 |
| Starch species | Pregelatinized starch (PD-1: Asahi Kasel Corporation) | 2.4 | — | — |
| | Corn starch (Corn Starch ST-C: Nippon Starch Chemical Co., Ltd.) | — | 2.4 | — |
| | Carboxymethyl starch sodium (EXPLOTAB: Kimura Sangyo Co., Ltd.) | — | — | 2.4 |

TABLE 2

| | | Amount blended (mg) (per tablet) | | | | |
|---|---|---|---|---|---|---|
| | Components | Example 4 | Example 9 | Example 10 | Example 11 | Example 12 |
| | Pemafibrate | 0.1 | 0.1 | 0.1 | 0.1 | 0.1 |
| Cellulose ether species | Croscarmellose sodium (KICCOLATE ND-2HS: Nichirin Chemical Industries, Ltd.) | 2.4 | — | — | — | — |
| | Carmellose sodium (Blanose: Ashland Ltd.) | — | 2.4 | — | — | — |
| | Low substituted hydroxypropylcellulose (L-HPC NBD-021: Shin-Etsu Chemical Co., Ltd.) | — | — | 2.4 | — | — |
| | Methylcellulose (METOLOSE SM-400: Shin-Etsu Chemical Co., Ltd.) | — | — | — | 2.4 | — |
| | Hydroxypropylmethylcellulose (TC-5E: Shin-Etsu Chemical Co., Ltd.) | — | — | — | — | 2.4 |
| | Lactose monohydrate | 92.3 | 92.3 | 92.3 | 92.3 | 92.3 |
| | Microcrystalline cellulose | 24 | 24 | 24 | 24 | 24 |
| | Magnesium stearate | 1.2 | 1.2 | 1.2 | 1.2 | 1.2 |
| | Total | 120 | 120 | 120 | 120 | 120 |
| | Pemafibrate content (ratio with respect to total mass of pharmaceutical composition: content in terms of a free form of pemafibrate) (mass %) | 0.083 | 0.083 | 0.083 | 0.083 | 0.083 |
| | Relative standard deviation (RSD) (%) | 2.7 | 2.0 | 4.9 | 3.0 | 1.4 |

The amount blended (mg) and the content (mass %) of pemafibrate in the table are values calculated from the amount added.

As is apparent from the results shown in Table 2, tablets containing, as a cellulose ether species, carmellose sodium, low substituted hydroxypropylcellulose, methylcellulose or hydroxypropylmethylcellulose instead of croscarmellose sodium (Examples 9 to 12) all had a small relative standard deviation and good uniformity of the content of pemafibrate per tablet. The amount of cellulose ether species added was as small as 2.4 mg (2 mass % with respect to the total mass of the tablet).

TABLE 3-continued

| | Amount blended (mg) (per tablet) | | |
|---|---|---|---|
| Components | Example 13 | Example 14 | Example 15 |
| Lactose monohydrate | 92.3 | 92.3 | 92.3 |
| Microcrystalline cellulose | 24 | 24 | 24 |
| Magnesium stearate | 1.2 | 1.2 | 1.2 |
| Total | 120 | 120 | 120 |

TABLE 3-continued

|  | Amount blended (mg) (per tablet) | | |
| --- | --- | --- | --- |
| Components | Example 13 | Example 14 | Example 15 |
| Pemafibrate content (ratio with respect to total mass of pharmaceutical composition:content in terms of a free form of pemafibrate) (mass %) | 0.083 | 0.083 | 0.083 |
| Relative standard deviation (RSD) (%) | 3.1 | 6.1 | 2.0 |

The amount blended (mg) and the content (mass %) of pemafibrate in the table are values calculated from the amount added.

As is apparent from the results shown in Table 3, tablets containing pregelatinized starch, corn starch or carboxymethyl starch sodium as a starch species (Examples 13 to 15) all had a small relative standard deviation and good uniformity of the content of pemafibrate per tablet as did the tablets of Examples 4 and 9 to 12 containing cellulose ether species in Test Example 2.

The above test results reveal that pharmaceutical compositions containing 0.017 to 4.2 mass % of pemafibrate, a salt thereof or a solvate thereof and starch species have good content uniformity.

Test Example 4

Content Uniformity Evaluation Test (4)

A test was conducted through the same method as in Test Example 2 except that tablets had compositions in which components and the amounts thereof were as shown in Table 4 below.

Table 4 shows the results.

TABLE 4

| Components | | Amount blended (mg) (per tablet) | |
| --- | --- | --- | --- |
| | | Example 16 | Example 17 |
| Pemafibrate | | 0.1 | 0.1 |
| Povidone species | Crospovidone (Polyplasdone XL: ISP Japan Ltd.) | 2.4 | — |
| | Polyvinyl pyrrolidone (Kollidon K-30: BASF Japan Ltd.) | — | 2.4 |
| Lactose monohydrate | | 92.3 | 92.3 |
| Microcrystalline cellulose | | 24 | 24 |
| Magnesium stearate | | 1.2 | 1.2 |
| Total | | 120 | 120 |
| Pemafibrate content (ratio with respect to total mass of pharmaceutical composition:content in terms of a free form of pemafibrate) (mass %) | | 0.083 | 0.083 |
| Relative standard deviation (RSD) (%) | | 2.8 | 7.6 |

The amount blended (mg) and the content (mass %) of pemafibrate in the table are values calculated from the amount added.

As is apparent from the results shown in Table 4, tablets containing crospovidone or polyvinyl pyrrolidone as a povidone species (Examples 16 and 17) all had a small relative standard deviation and good uniformity of the content of pemafibrate per tablet as did the tablets of Examples 4 and 9 to 12 containing cellulose ether species in Test Example 2.

The above test results reveal that pharmaceutical compositions containing 0.017 to 4.2 mass % of pemafibrate, a salt thereof or a solvate thereof and povidone species have good content uniformity.

Test Example 5

Content Uniformity Evaluation Test (5)

A test was conducted through the same method as in Test Example 2 except that tablets had compositions in which components and the amounts thereof were as shown in Table 5 below.

Table 5 shows the results.

TABLE 5

| Components | | Amount blended (mg) (per tablet) | |
| --- | --- | --- | --- |
| | | Example 18 | Example 19 |
| Pemafibrate | | 0.1 | 0.1 |
| Silicic acid compounds | Hydrous magnesium silicate (Talc: Nippon Talc Co., Ltd.) | 2.4 | — |
| | Hydrated silicon dioxide (Adsolider 102: Freund Corporation) | — | 2.4 |
| Lactose monohydrate | | 92.3 | 92.3 |
| Microcrystalline cellulose | | 24 | 24 |
| Magnesium stearate | | 1.2 | 1.2 |
| Total | | 120 | 120 |
| Pemafibrate content (ratio with respect to total mass of pharmaceutical composition:content in terms of a free form of pemafibrate) (mass %) | | 0.083 | 0.083 |
| Relative standard deviation (RSD) (%) | | 3.1 | 6.6 |

The amount blended (mg) and the content (mass %) of pemafibrate in the table are values calculated from the amount added.

As is apparent from the results shown in Table 5, tablets containing hydrous magnesium silicate or hydrated silicon dioxide as a silicic acid compound (Examples 18 and 19) all had a small relative standard deviation and good uniformity of the content of pemafibrate per tablet as did the tablets of Examples 4 and 9 to 12 containing cellulose ether species in Test Example 2.

The above test results reveal that pharmaceutical compositions containing 0.017 to 4.2 mass % of pemafibrate, a salt thereof or a solvate thereof and silicic acid compounds have good content uniformity.

Test Example 6

Content Uniformity Evaluation Test (6)

A test was conducted through the same method as in Test Example 6 except that tablets had compositions in which components and the amounts thereof were as shown in Table 6 below.

Table 6 shows the results.

TABLE 6

| Components | Amount blended (mg) (per tablet) Example 20 |
| --- | --- |
| Pemafibrate | 0.1 |
| Macrogol 6000 (Macrogol 6000: NOF CORPORATION) | 2.4 |
| Lactose monohydrate | 92.3 |
| Microcrystalline cellulose | 24 |
| Magnesium stearate | 1.2 |
| Total | 120 |

TABLE 6-continued

| Components | Amount blended (mg) (per tablet) Example 20 |
|---|---|
| Pemafibrate content (ratio with respect to total mass of pharmaceutical composition:content in terms of a free form of pemafibrate) (mass %) | 0.083 |
| Relative standard deviation (RSD) (%) | 1.7 |

The amount blended (mg) and the content (mass %) of pemafibrate in the table are values calculated from the amount added.

As is apparent from the results shown in Table 6, tablets containing macrogol as a polyhydric alcohol (Example 20) all had a small relative standard deviation and good uniformity of the content of pemafibrate per tablet as did the tablets of Examples 4 and 9 to 12 containing cellulose ether species in Test Example 2.

The above test results reveal that pharmaceutical compositions containing 0.017 to 4.2 mass % of pemafibrate, a salt thereof or a solvate thereof and polyhydric alcohols have good content uniformity.

Test Example 7

Content uniformity evaluation test (7) A test was conducted through the same method as in Test Example 6 except that tablets had compositions in which components and the amounts thereof were as shown in Table 7 below.

Table 7 shows the results.

TABLE 7

| Components | Amount blended (mg) (per tablet) Example 21 |
|---|---|
| Pemafibrate | 0.1 |
| Sodium lauryl sulfate (Sodium Lauryl Sulfate: Wako Pure Chemical Industries, Ltd.) | 2.4 |
| Lactose monohydrate | 92.3 |
| Microcrystalline cellulose | 24 |
| Magnesium stearate | 1.2 |
| Total | 120 |
| Pemafibrate content (ratio with respect to total mass of pharmaceutical composition:content in terms of a free form of pemafibrate) (mass %) | 0.083 |
| Relative standard deviation (RSD) (%) | 1.0 |

The amount blended (mg) and the content (mass %) of pemafibrate in the table are values calculated from the amount added.

As is apparent from the results shown in Table 7, tablets containing sodium lauryl sulfate as an alkyl sulfate ester (Example 21) all had a small relative standard deviation and good uniformity of the content of pemafibrate per tablet as did the tablets of Examples 4 and 9 to 12 containing cellulose ether species in Test Example 2.

The above test results reveal that pharmaceutical compositions containing 0.017 to 4.2 mass % of pemafibrate, a salt thereof or a solvate thereof and an alkyl sulfate ester have good content uniformity.

Test Example 8

Content Uniformity Evaluation Test (8)

The following test was conducted for evaluating the uniformity of the content of pemafibrate in a pharmaceutical composition.

The tablets of Examples 22 to 25 were produced using the components shown in Table 8 in such a manner that the amounts (mg) of the components per tablet were as shown in Table 8. Specific procedures will be described below.

Example 22

Pemafibrate, lactose monohydrate, croscarmellose sodium and hydroxypropylcellulose were mixed for 5 minutes, purified water was then added, and the mixture was kneaded for 3 minutes, granulated, dried, and then subjected to grain size adjustment to obtain a granulation product. Magnesium stearate was mixed with the obtained granulation product, and the mixture was then pelletized to produce 10,000 tablets each having a weight of 120 mg.

Example 23

10,000 tablets each having a weight of 120 mg were produced through the same method as in Example 22 except that the lactose monohydrate was partially replaced by microcrystalline cellulose.

Example 24

10,000 tablets each having a weight of 120 mg were produced through the same method as in Example 23 except that the lactose monohydrate was all replaced by mannitol.

Example 25

10,000 tablets each having a weight of 120 mg were produced through the same method as in Example 22 except that the lactose monohydrate was all replaced by microcrystalline cellulose.

From the obtained tablets, ten tablets were randomly picked up, and the content of pemafibrate in each tablet was measured through the same method as in Test Example 1. From the thus-obtained measured value of the pemafibrate content per tablet, a relative standard deviation (RSD) (%) of the pemafibrate content in the tablet was calculated in accordance with The Japanese Pharmacopoeia, 17th Edition, Content Uniformity Test, and used as an index of variation (degree of uniformity) of the pemafibrate content in the tablet.

Table 8 shows the results.

TABLE 8

| | Amount blended (mg) (per tablet) | | | |
|---|---|---|---|---|
| Components | Example 22 | Example 23 | Example 24 | Example 25 |
| Pemafibrate | 0.1 | 0.1 | 0.1 | 0.1 |
| Lactose monohydrate (Pharmatose 200M: DFE Pharma) | 110.3 | 98.3 | — | — |
| Mannitol (Mannit P: Mitsubishi Shoji Foodtech Co., ltd) | — | — | 98.3 | — |
| Microcrystalline cellulose (CEOLUS PH-102: Asahi Kasei Corporation) | — | 12.0 | 12.0 | 110.3 |
| Croscarmellose sodium (KICCOLATE ND-2HS: Nichirin Chemical Industries, Ltd.) | Balance | Balance | Balance | Balance |
| Hydroxypropylcellulose (HPC-L: Nippon Soda Co., Ltd.) | | | | |
| Magnesium stearate | | | | |
| Total | 120 | 120 | 120 | 120 |

TABLE 8-continued

| Components | Amount blended (mg) (per tablet) | | | |
|---|---|---|---|---|
| | Example 22 | Example 23 | Example 24 | Example 25 |
| Pemafibrate content (ratio with respect to total mass of pharmaceutical composition:content in terms of a free form of pemafibrate) (mass %) | 0.083 | 0.083 | 0.083 | 0.083 |
| Relative standard deviation (RSD) (%) | 1.6 | 1.4 | 2.2 | 4.0 |

The amount blended (mg) and the content (mass %) of pemafibrate in the table are values calculated from the amount added.

As is apparent from the results shown in Table 8, tablets containing lactose monohydrate as a disaccharide species (Examples 22 and 23), tablets containing mannitol as a polyhydric alcohol (Example 24), and tablets containing microcrystalline cellulose as cellulose (Example 25) all had a small relative standard deviation and good uniformity of the content of pemafibrate per tablet.

The above test results reveal that pharmaceutical compositions containing 0.017 to 4.2 mass % of pemafibrate, a salt thereof or a solvate thereof and one or more selected from the group consisting of a disaccharide, a polyhydric alcohol and cellulose have good content uniformity.

Production Examples 1 to 6

Tablets can be conventionally produced using the components shown in Table 9 in such a manner that the amounts (mg) of the components contained per tablet are as shown in Table 9.

TABLE 9

| Components | Amount blended (mg) (per tablet) | | | | | |
|---|---|---|---|---|---|---|
| | Production Example 1 | Production Example 2 | Production Example 3 | Production Example 4 | Production Example 5 | Production Example 6 |
| Pemafibrate | 0.03 | 0.1 | 0.2 | 1 | 2 | 3 |
| Lactose monohydrate | q.s. | q.s. | q.s. | q.s. | q.s. | q.s. |
| Microcrystalline cellulose | 20 | 20 | 20 | 20 | 20 | 20 |
| Croscarmellose sodium | 2 | 2 | 2 | 2 | 2 | 2 |
| Magnesium stearate | 1 | 1 | 1 | 1 | 1 | 1 |
| Total | 100 mg | 100 mg | 100 mg | 100 mg | 100 mg | 100 mg |
| Pemafibrate content (ratio with respect to total mass of pharmaceutical composition: content in terms of a free form of pemafibrate) (mass %) | 0.03 | 0.1 | 0.2 | 1 | 2 | 3 |

The amount blended (mg) and the content (mass %) of pemafibrate in the table are values calculated from the amount added.

Production Examples 7 to 12

Tablets can be conventionally produced through a wet grain compression method using the components shown in Tables 10 and 11 in such a manner that the amounts (mg) of the components contained per tablet are as shown in Tables 10 and 11.

TABLE 10

| Components | Amount blended (mg) (per tablet) | | |
|---|---|---|---|
| | Production Example 7 | Production Example 8 | Production Example 9 |
| Pemafibrate | 0.05 | 0.8 | 4 |
| Lactose monohydrate | q.s. | q.s. | q.s. |
| Magnesium stearate | 1.2 | 1.2 | 1.2 |
| Carmellose sodium | 3 | | 6 |
| Croscarmellose sodium | 1 | | |
| Low substituted hydroxypropylcellulose | | 2 | 4 |
| Crospovidone | | 3 | |
| Carmellose calcium | 2 | | |
| Povidone K25 | | 4 | |
| Ethylcellulose | | 5 | |
| Hydroxyethylmethylcellulose | | 1 | |
| Hypromellose acetate succinate | | | 4 |
| Hypromellose phthalate | | | 6 |
| Hydroxyethylcellulose | 1 | | 2 |
| Hydroxypropylcellulose | 1 | | |
| Hypromellose | | 4 | |
| Methylcellulose | 1 | | |
| Polyvinyl alcohol (partially saponified) | | | 1 |
| Magnesium aluminosilicate | | | 3 |
| Aluminum magnesium silicate | | | 2 |
| Total | 100 mg | 100 mg | 100 mg |
| Pemafibrate content (ratio with respect to total mass of pharmaceutical composition:content in terms of a free form of pemafibrate) (mass %) | 0.05 | 0.8 | 4 |

The amount blended (mg) and the content (mass %) of pemafibrate in the table are values calculated from the amount added.

TABLE 11

| Components | Amount blended (mg) (per tablet) | | |
|---|---|---|---|
| | Production Example 10 | Production Example 11 | Production Example 12 |
| Pemafibrate | 0.025 | 0.4 | 2 |
| Lactose monohydrate | q.s. | q.s. | q.s. |

TABLE 11-continued

| Components | Production Example 10 | Production Example 11 | Production Example 12 |
|---|---|---|---|
| Magnesium stearate | 1.2 | 1.2 | 1.2 |
| Carmellose sodium | | | 1 |
| Croscarmellose sodium | 2 | | 1 |
| Carmellose | | 5 | |
| Carmellose potassium | | | 3 |
| Povidone K90 | 4 | | |
| Copolyvidone | | 3 | |
| Hydroxyethylmethylcellulose | | 9 | |
| Hypromellose acetate succinate | | | 2 |
| Carboxymethylethylcellulose | 5 | | 2 |
| Hydroxypropylcellulose | 1 | | |
| Hypromellose | | 0.5 | |
| Methylcellulose | | | 1 |
| Potato starch | | 15 | |
| Macrogol 400 | | | 2 |
| Macrogol 4000 | | | 2 |
| Macrogol 6000 | | 6 | |
| Polyvinyl alcohol (fully saponified) | 1 | | |
| Calcium silicate | 1 | | |
| Hydrous magnesium silicate | | 5 | |
| Magnesium aluminometasilicate | | 1 | |
| Meglumine | | | 0.5 |
| Bentonite | | | 6 |
| Total | 100 mg | 100 mg | 100 mg |
| Pemafibrate content (ratio with respect to total mass of pharmaceutical composition:content in terms of a free form of pemafibrate) (mass %) | 0.025 | 0.4 | 2 |

The amount blended (mg) and the content (mass %) of pemafibrate in the table are values calculated from the amount added.

Production Examples 13 to 18

Tablets can be conventionally produced through a direct powder compression method using the components shown in Tables 12 and 13 in such a manner that the amounts (mg) of the components contained per tablet are as shown in Tables 12 and 13.

TABLE 12

| Components | Production Example 13 | Production Example 14 | Production Example 15 |
|---|---|---|---|
| Pemafibrate | 0.1 | 0.4 | 1 |
| Lactose monohydrate | q.s. | q.s. | q.s. |
| Magnesium stearate | 1.2 | 1.2 | 1.2 |
| Pregelatinized starch | 3 | | |
| Wheat starch | 15 | | |
| Rice starch | | 10 | |
| Corn starch | | 20 | |
| Partially pregelatinized starch | | | 3 |
| Wheat flour | | | 10 |
| Hydrated silicon dioxide | | 1 | |
| Amorphous silicon oxide hydrate | | | 0.5 |
| Kaolin | | | 0.4 |
| Talc | 5 | | |
| Sodium lauryl sulfate | 0.3 | | |
| Erythritol | 20 | | |
| Xylitol | | 30 | |
| D-mannitol | | | 40 |
| Propylene glycol | | | 1 |
| Total | 100 mg | 100 mg | 100 mg |
| Pemafibrate content (ratio with respect to total mass of pharmaceutical composition:content in terms of a free form of pemafibrate) (mass %) | 0.1 | 0.4 | 1 |

The amount blended (mg) and the content (mass %) of pemafibrate in the table are values calculated from the amount added.

TABLE 13

| Components | Production Example 16 | Production Example 17 | Production Example 18 |
|---|---|---|---|
| Pemafibrate | 0.3 | 0.6 | 0.9 |
| Lactose monohydrate | q.s. | q.s. | q.s. |
| Magnesium stearate | 1.2 | 1.2 | 1.2 |
| Pregelatinized starch | | | 2 |
| Partially pregelatinized starch | | | 6 |
| Rice flour | 10 | | |
| Semi-digested starch | 5 | | |
| Hydroxypropyl starch | | 8 | 1 |
| Carboxymethyl starch sodium (sodium carboxymethyl starch) | | 3 | |
| Light anhydrous silicic acid | 2 | | |
| heavy anhydrous silicic acid | | 0.3 | |
| Silicon dioxide | | | 0.1 |
| Natural aluminum silicate | | | 0.8 |
| Synthetic aluminum silicate | | 0.7 | |
| Diatomaceous earth | 0.2 | | |
| D-sorbitol | 50 | | |
| Maltitol | | 60 | |
| Lactitol | | | 70 |
| Polyoxyethylene (105) polyoxypropylene (5) glycol | | 0.5 | |
| Polyoxyethylene (160) polyoxypropylene (30) glycol | | | 2 |
| Total | 100 mg | 100 mg | 100 mg |
| Pemafibrate content (ratio with respect to total mass of pharmaceutical composition:content in terms of a free form of pemafibrate) (mass %) | 0.3 | 0.6 | 0.9 |

The amount blended (mg) and the content (mass %) of pemafibrate in the table are values calculated from the amount added.

Production Examples 19 to 21

Tablets can be conventionally produced through a wet grain compression method using the components shown in Table 14 in such a manner that the amounts (mg) of the components contained per tablet are as shown in Table 14.

TABLE 14

| | Amount blended (mg) (per tablet) | | |
|---|---|---|---|
| | Production Example 19 | Production Example 20 | Production Example 21 |
| Pemafibrate | 0.06 | 0.3 | 1.5 |
| Corn starch | q.s. | q.s. | q.s. |
| Hydroxypropylmethyl-cellulose | 10 | 20 | 5 |
| Polyvinylpyrrolidone | 5 | 5 | 5 |
| Magnesium stearate | 1 | 1 | 1 |
| Lactose monohydrate | 20 | | |
| Trehalose hydrate | | 30 | |
| Sucralose | | | 50 |
| Reduced maltose starch syrup | | | |
| Microcrystalline cellulose | | | |
| Total | 100 mg | 100 mg | 100 mg |
| Pemafibrate content (ratio with respect to total mass of pharmaceutical composition: content in terms of a free form of pemafibrate) (mass %) | 0.06 | 0.3 | 1.5 |

The amount blended (mg) and the content (mass %) of pemafibrate in the table are values calculated from the amount added.

Production Examples 22 to 24

Tablets can be conventionally produced through a direct powder compression method using the components shown in Table 15 in such a manner that the amounts (mg) of the components contained per tablet are as shown in Table 15.

TABLE 15

| | Amount blended (mg) (per tablet) | | |
|---|---|---|---|
| | Production Example 22 | Production Example 23 | Production Example 24 |
| Pemafibrate | 0.07 | 0.7 | 1.4 |
| Corn starch | q.s. | q.s. | q.s. |
| Magnesium stearate | 1 | 1 | 1 |
| Lactose monohydrate | 60 | | 5 |
| Trehalose hydrate | | | 5 |
| Sucralose | | | 5 |
| Reduced maltose starch syrup | | 40 | 5 |
| Microcrystalline cellulose | 5 | 15 | 25 |
| Total | 100 mg | 100 mg | 100 mg |
| Pemafibrate content (ratio with respect to total mass of pharmaceutical composition: content in terms of a free form of pemafibrate) (mass %) | 0.07 | 0.7 | 1.4 |

The amount blended (mg) and the content (mass %) of pemafibrate in the table are values calculated from the amount added.

Production Examples 25 to 30

Tablets can be conventionally produced using the components shown in Table 16 in such a manner that the amounts (mg) of the components contained per tablet are as shown in Table 16.

TABLE 16

| | Amount blended (mg) (per tablet) | | | | | |
|---|---|---|---|---|---|---|
| Components | Production Example 25 | Production Example 26 | Production Example 27 | Production Example 28 | Production Example 29 | Production Example 30 |
| Pemafibrate | 0.1 | 0.4 | 0.1 | 0.2 | 0.4 | 0.2 |
| Lactose monohydrate | q.s. | q.s. | q.s. | q.s. | q.s. | q.s. |
| Magnesium stearate | 1.2 | 1.2 | 1.2 | 1.2 | 1.2 | 1.2 |
| Carmellose sodium | 3 | | 6 | | | 1 |
| Croscarmellose sodium | 1 | | | 2 | | 1 |
| Low substituted hydroxypropylcellulose | | 2 | 4 | | | |
| Carmellose | | 3 | | 6 | | |
| Carmellose potassium | 3 | | | | 5 | |
| Carmellose calcium | | 2 | | 2 | 5 | 3 |
| Hydroxyethylcellulose | 1 | | 2 | | | |
| Hydroxypropylcellulose | 1 | | | 1 | | |
| Hypromellose | | 1 | | | 0.5 | |
| Methylcellulose | 1 | | | | | 1 |
| Microcrystalline cellulose | | 5 | | | | 40 |
| Powdered cellulose | 50 | | | | | |
| Cellulose acetate phthalate | 3 | | | | 4 | |
| Ethylcellulose | | 5 | | | | |
| Hydroxyethylmethylcellulose | | 1 | | | 9 | |
| Hypromellose acetate succinate | | | 4 6 | | | 2 |
| Hypromellose phthalate | | | | | 5 | 2 |
| Carboxymethylethylcellulose | | | | | | |
| Total | 100 mg | 100 mg | 100 mg | 100 mg | 100 mg | 100 mg |
| Pemafibrate content (ratio with respect to total mass of pharmaceutical composition: content in terms of a free form of pemafibrate) (mass %) | 0.1 | 0.4 | 0.1 | 0.2 | 0.4 | 0.2 |

The amount blended (mg) and the content (mass %) of pemafibrate in the table are values calculated from the amount added.

INDUSTRIAL APPLICABILITY

The present invention enables provision of a pharmaceutical composition having excellent homogeneity and containing pemafibrate which exhibits plasma triglyceride concentration reducing action, HDL cholesterol increasing action, etc. The pharmaceutical composition can be used in, for example, pharmaceutical preparation industries.

The invention claimed is:

1. A solid pharmaceutical dosage form composition comprising pharmaceutically acceptable additives and consisting of pemafibrate, a salt thereof or a solvate thereof as the pharmaceutically active component in an amount of 0.017 to 4.2 mass % in terms of a free form of pemafibrate with respect to the total mass of the pharmaceutical composition.

2. The pharmaceutical composition according to claim 1, wherein the dosage form of the composition is a tablet, a capsule, a granule, a powder or a pill.

3. The solid pharmaceutical composition according to claim 1, comprising one or more members selected from the group selected from the group consisting of a cellulose ether species, a starch species, a povidone species, a silicic acid compound, a polyhydric alcohol, an alkyl sulfate ester, a disaccharide species and cellulose.

4. The pharmaceutical composition according to claim 3, wherein the cellulose ether species is one or more selected from the group consisting of an alkylcellulose, a hydroxyalkylcellulose, an alkyl(hydroxyalkyl)cellulose, a carboxyalkylcellulose, a cross-linked polymer of a carboxyalkylcellulose and a salt thereof.

5. The pharmaceutical composition according to claim 3, wherein the cellulose ether species is one or more selected from the group consisting of a C1-C6 alkylcellulose, a hydroxy C1-C6 alkylcellulose, a C1-C6 alkyl(hydroxy C1-C6 alkyl)cellulose, a carboxy C1-C6 alkylcellulose, a cross-linked polymer of a carboxy C1-C6 alkylcellulose and a salt thereof.

6. The pharmaceutical composition according to claim 3, wherein the cellulose ether species is one or more selected from the group consisting of methylcellulose, ethylcellulose, hydroxypropylcellulose, hypromellose, carmellose, carmellose potassium, carmellose calcium, carmellose sodium and croscarmellose sodium.

7. The pharmaceutical composition according to claim 3, wherein the starch species is one or more selected from the group consisting of starch, a hydroxyalkyl ether of starch, a carboxyalkyl ether of starch and a salt thereof.

8. The pharmaceutical composition according to claim 3, wherein the starch species is one or more selected from the group consisting of starch, a hydroxy C1-C6 alkyl ether of starch, a carboxy C1-C6 alkyl ether and a salt thereof.

9. The pharmaceutical composition according to claim 4, wherein the starch species is one or more selected from the group consisting of starch, hydroxypropyl starch, carboxymethyl starch and a salt thereof.

10. The pharmaceutical composition according to claim 4, wherein the povidone species is one or more selected from the group consisting of povidone and crospovidone.

11. The pharmaceutical composition according to claim 4, wherein the silicic acid compound is one or more selected from the group consisting of a hydrous silicic acid compound, a salt of a hydrous silicic acid compound, anhydrous silicic acid and a salt of anhydrous silicic acid.

12. The pharmaceutical composition according to claim 4, wherein the silicic acid compound is one or more selected from the group consisting of hydrous magnesium silicate, hydrated silicon dioxide and light anhydrous silicic acid.

13. The pharmaceutical composition according to claim 4, wherein the polyhydric alcohol is one or more selected from the group consisting of macrogol, erythritol, xylitol, mannitol, sorbitol, maltitol and lactitol.

14. The pharmaceutical composition according to claim 4, wherein the alkyl sulfate ester salt is one or more selected from the group consisting of a lauryl sulfate ester salt, a tetradecyl sulfate ester salt, a hexadecyl sulfate ester salt and an octadecyl sulfate ester salt.

15. The pharmaceutical composition according to claim 4, wherein the alkyl sulfate ester salt is sodium lauryl sulfate.

16. The pharmaceutical composition according to claim 4, wherein the disaccharide species is one or more selected from the group consisting of sucrose, lactulose, lactose, maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, primevelose, sucralose and a solvate thereof.

17. The pharmaceutical composition according to claim 3, wherein the disaccharide species is one or more selected from the group consisting of sucrose, lactose, maltose, trehalose, palatinose, sucralose and a solvate thereof.

18. The pharmaceutical composition according to claim 3, wherein the cellulose is one or more selected from the group consisting of cellulose and a salt thereof.

* * * * *